US011020600B2

(12) United States Patent
Schmidt et al.

(10) Patent No.: US 11,020,600 B2
(45) Date of Patent: *Jun. 1, 2021

(54) IMPLANTABLE MEDICAL DEVICE WITH RADIOPAQUE ID TAG

(71) Applicant: CARDIAC PACEMAKERS, INC., St. Paul, MN (US)

(72) Inventors: Brian L. Schmidt, White Bear Lake, MN (US); Bryan J. Swackhamer, Shoreview, MN (US); Robert Allen Jones, Lake Elmo, MN (US); Steven A. Kubow, Hugo, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 402 days.

This patent is subject to a terminal disclaimer.

(21) Appl. No.: 16/042,616

(22) Filed: Jul. 23, 2018

(65) Prior Publication Data
US 2018/0326218 A1   Nov. 15, 2018

Related U.S. Application Data

(63) Continuation of application No. 15/018,379, filed on Feb. 8, 2016, now Pat. No. 10,046,167.
(Continued)

(51) Int. Cl.
*A61N 1/375* (2006.01)
*A61N 1/362* (2006.01)
(Continued)

(52) U.S. Cl.
CPC ............ *A61N 1/3756* (2013.01); *A61B 90/94* (2016.02); *A61N 1/362* (2013.01); *A61N 1/37* (2013.01);
(Continued)

(58) Field of Classification Search
CPC ...... A61N 1/375; A61N 1/3756; A61N 1/362; A61N 1/37; A61B 90/94; A61L 31/18
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Alyssa M Alter
(74) *Attorney, Agent, or Firm* — Seager, Tufte & Wickhem LLP.

(57) ABSTRACT

An implantable medical device includes a housing. A first ID tag is secured relative to the housing at a first position and defines a first radiopaque manufacturer code section that visually identifies a manufacturer of the implantable medical device. A second ID tag is secured relative to the housing at a second position that is offset from the first position in at least one dimension. The second ID tag defines a second radiopaque manufacturer code section that also visually identifies the manufacturer of the implantable medical device.

13 Claims, 26 Drawing Sheets

Related U.S. Application Data

(60) Provisional application No. 62/138,799, filed on Mar. 26, 2015, provisional application No. 62/113,827, filed on Feb. 9, 2015.

(51) Int. Cl.
  *A61B 90/94* (2016.01)
  *A61N 1/37* (2006.01)
  *A61L 31/18* (2006.01)

(52) U.S. Cl.
  CPC ..... *A61N 1/37512* (2017.08); *A61N 1/37518* (2017.08); *A61L 31/18* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |

(56) References Cited

U.S. PATENT DOCUMENTS

| | | |
|---|---|---|
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |

(56) References Cited

U.S. PATENT DOCUMENTS

| | | |
|---|---|---|
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |

(56) References Cited

U.S. PATENT DOCUMENTS

| | | |
|---|---|---|
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |

(56) References Cited

U.S. PATENT DOCUMENTS

| | | |
|---|---|---|
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 10,046,167 B2 * | 8/2018 | Schmidt ............... A61N 1/3756 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |

(56) References Cited

U.S. PATENT DOCUMENTS

| | | |
|---|---|---|
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0023343 A1 | 2/2011 | Turner et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0065503 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |

(56) References Cited

U.S. PATENT DOCUMENTS

| | | |
|---|---|---|
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhurst et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |

(56) References Cited

U.S. PATENT DOCUMENTS

| | | |
|---|---|---|
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 0534782 A1 | 3/1993 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2005105201 A2 | 11/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2010126877 A1 | 11/2010 |
| WO | 2012054102 A1 | 4/2012 |
| WO | 2013080038 A2 | 6/2013 |
| WO | 2013082289 A1 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

International Search Report and Written Opinion for Application No. PCT/US2016/017002, 6 pages, dated Aug. 24, 2016.

Invitation to Pay Additional Fees and, Where Applicable, Protest Fee, PCT No. PCT/US2016/017002, 6 pages, dated May 23, 2016.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

* cited by examiner

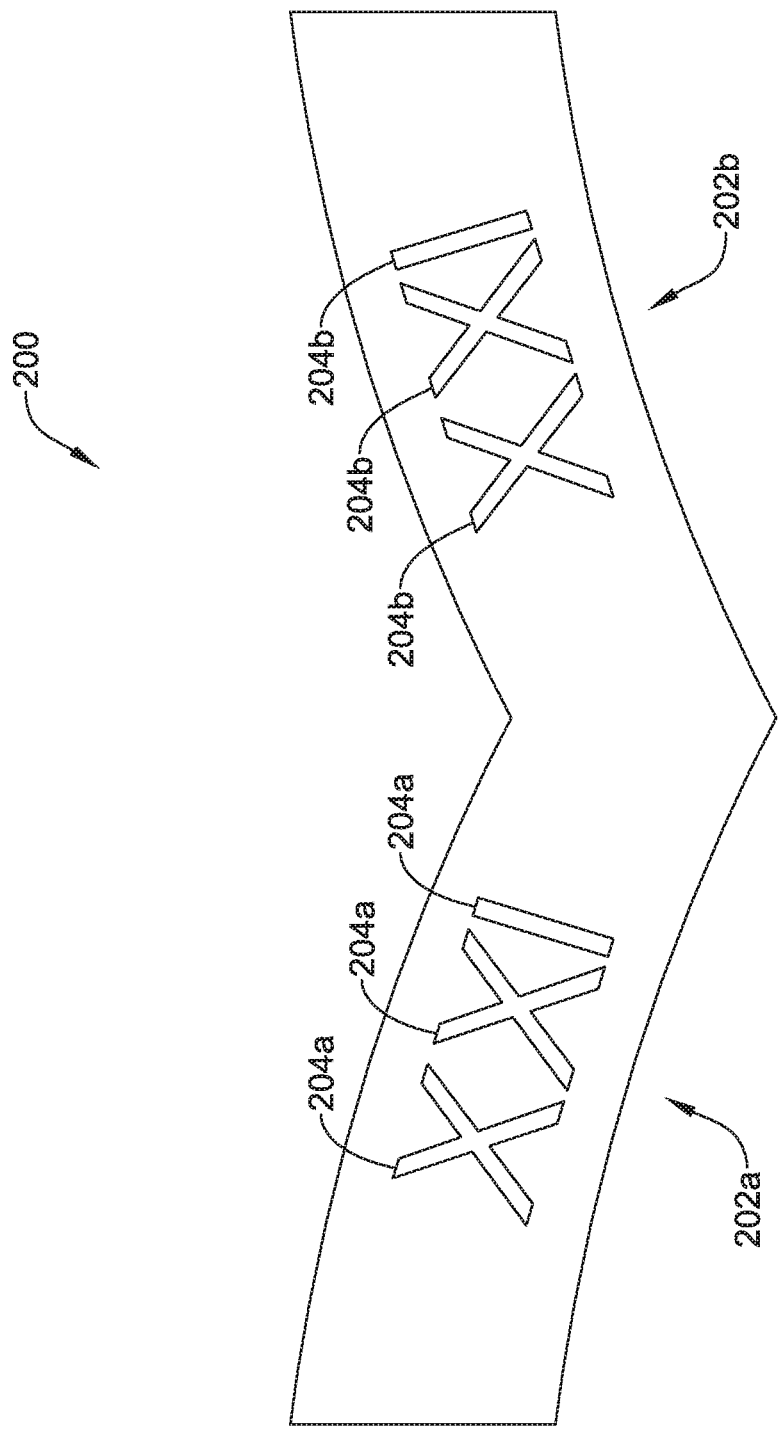

0
IMPLANTABLE MEDICAL DEVICE WITH RADIOPAQUE ID TAG

CROSS REFERENCE TO RELATED APPLICATIONS

This application is a continuation of co-pending U.S. patent application Ser. No. 15/018,379, filed Feb. 8, 2016 and entitled "Implantable Medical Device With Radiopaque ID Tag", which claims the benefit of U.S. Provisional Patent Application Ser. No. 62/113,827 filed on Feb. 9, 2015, and also claims the benefit of U.S. Provisional Patent Ser. No. 62/138,799 filed on Mar. 26, 2015, all of which are incorporated herein by reference.

TECHNICAL FIELD

The present disclosure generally relates to implantable medical devices, and more particularly, to implantable medical devices that include a radiopaque ID tag that provides identifying information regarding the implantable medical device during an imaging process such as an x-ray.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, implantable neurostimulators are used to provide neurostimulation therapy to a patient. In yet another example, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various devices (e.g., pacemakers, defibrillators, etc.) are often implanted in a patient's body. Such devices may monitor and provide electrical stimulation to the heart to help the heart operate in a more normal, efficient and/or safe manner. In some applications, it may be beneficial for the implantable medical devices to include a radiopaque ID tag that permits identification of the implantable medical device during an imaging process such as an x-ray.

SUMMARY

The present disclosure generally relates to implantable medical devices, and more particularly, to implantable medical devices including one or more radiopaque ID tags that provide identifying information regarding the implantable medical device during an imaging process such as an x-ray.

An example implantable medical device may include: a housing, a first ID tag secured relative to the housing at a first position, wherein the first ID tag defines a first radiopaque manufacturer code section that visually identifies a manufacturer of the implantable medical device, and a second ID tag secured relative to the housing at a second position, wherein the second position is offset from the first position in at least one dimension. The second ID tag may define a second radiopaque manufacturer code section that also visually identifies the manufacturer of the implantable medical device.

Alternatively or additionally to the embodiments above, the first radiopaque manufacturer code section and the second radiopaque manufacturer code section may each define one or more radiopaque alphanumeric characters.

Alternatively or additionally to any of the embodiments above, the one or more radiopaque alphanumeric characters may be configured to be human readable in an x-ray or other image of the implantable medical device.

Alternatively or additionally to any of the embodiments above, the first radiopaque manufacturer code section of the first ID tag may be structured to define a first radiopaque manufacturer code as well as a reverse image of the first radiopaque manufacturer code.

Alternatively or additionally to any of the embodiments above, at least one of the first ID tag and the second ID tag are disposed on an outer surface of the housing.

Alternatively or additionally to any of the embodiments above, at least one of the first ID tag and the second ID tag are disposed on an internal component located within the housing.

Alternatively or additionally to any of the embodiments above, the second position is offset from the first position in at least two dimensions.

Alternatively or additionally to any of the embodiments above, the housing has a cylinder along at least part of its length that includes the first position and the second position, and the second position is axially offset and radially offset from the first position.

Alternatively or additionally to any of the embodiments above, the first ID tag and the second ID tag may comprise portions of a helix structure that traverses along at least part of a length of the housing.

Alternatively or additionally to any of the embodiments above, the implantable medical device further comprises a battery, wherein at least one of the first ID tag and the second ID are disposed on or within a component of the battery.

Alternatively or additionally to any of the embodiments above, the implantable medical device further comprises a circuit board, wherein at least one of the first ID tag and the second ID tag is secured to the circuit board.

Alternatively or additionally to any of the embodiments above, the circuit board comprises at least two layers, and wherein at least one of the first ID tag and the second ID tag is positioned between two of the layers of the circuit board.

In one example, the implantable medical device may be a leadless cardiac pacemaker. In some instances, the leadless cardiac pacemaker may comprise: an elongated housing defining an energy storage section and a circuit section, an energy source disposed within the energy storage section, a circuit board disposed within the circuit section and operably coupled to the energy source, and an ID tag secured relative to the elongated housing, wherein the ID tag is configured to define a radiopaque manufacturer code that visually identifies a manufacturer of the leadless cardiac pacemaker. In some cases, two or more individual ID tags may be secured relative to the elongated housing, sometimes offset from one another in at least two dimensions.

Alternatively or additionally to any of the embodiments above, the leadless cardiac pacemaker may further comprise an insulative coating disposed over the elongated housing, and an ID tag may be covered by the insulative coating.

Alternatively or additionally to any of the embodiments above, an ID tag may be secured to the elongated housing.

Alternatively or additionally to any of the embodiments above, the energy source may comprise a battery with a battery liner, an anode disposed within the battery liner, and a cathode disposed within the anode. An ID tag may be disposed on or in one of the battery liner, the anode and the cathode.

Alternatively or additionally to any of the embodiments above, the leadless cardiac pacemaker may further comprise a battery pin extending from cathode of the energy source, wherein an ID tag may be disposed on or in the battery pin.

Alternatively or additionally to any of the embodiments above, the leadless cardiac pacemaker may further comprise a desiccant, wherein an ID tag may be disposed on or in the desiccant.

Alternatively or additionally to any of the embodiments above, the leadless cardiac pacemaker may further comprise an overmolding, wherein an ID tag may be disposed on or in the overmolding.

Alternatively or additionally to any of the embodiments above, the leadless cardiac pacemaker may further comprises a drug collar, wherein an ID tag may be disposed on or in the drug collar.

Alternatively or additionally to any of the embodiments above, the elongated housing may comprise a proximal end feature for retrieval of the leadless cardiac pacemaker, and an ID tag may be secured to the proximal end feature.

Alternatively or additionally to any of the embodiments above, the leadless cardiac pacemaker may further comprise an axial rotation marker, and an ID tag may be disposed within or by a cutout formed in the axial rotation marker.

Alternatively or additionally to any of the embodiments above, an ID tag may be formed from a platinum wire disposed within a slot formed in the housing or other component of the leadless cardiac pacemaker.

Alternatively or additionally to any of the embodiments above, an ID tag may define an alphanumeric code that is readable by an individual during an imaging process.

Alternatively or additionally to any of the embodiments above, an ID tag may comprises an etched, machined, cut, or sintered ID tag.

Alternatively or additionally to any of the embodiments above, an ID tag may comprise a molded ID tag.

Alternatively or additionally to any of the embodiments above, an ID tag may comprise a radiopaque ink.

In another example, a leadless cardiac pacemaker may comprise: an elongated housing extending along a central axis, and an ID tag system secured relative to the elongated housing. The ID tag system may comprise a first radiopaque manufacturer code section that visually identifies a manufacturer of the implantable medical device and a second radiopaque manufacturer code section that also visually identifies the manufacturer of the implantable medical device. In some cases, the first radiopaque manufacturer code section and the second radiopaque manufacturer code section may face different radial directions relative to the central axis of the elongated housing of the leadless cardiac pacemaker.

Alternatively or additionally to any of the embodiments above, the first radiopaque manufacturer code section is the same as the second radiopaque manufacturer code section.

Alternatively or additionally to any of the embodiments above, the first radiopaque manufacturer code section may be a mirror image of the second radiopaque manufacturer code section.

Alternatively or additionally to any of the embodiments above, the first radiopaque manufacturer code section and the second radiopaque manufacturer code section may be part of a common piece.

Alternatively or additionally to any of the embodiments above, the first radiopaque manufacturer code section may be a separate piece from the second radiopaque manufacturer code section.

Alternatively or additionally to any of the embodiments above, the first radiopaque manufacturer code section may be mechanically connected to the second radiopaque manufacturer code section before and after being secured relative to the elongated housing.

Alternatively or additionally to any of the embodiments above, the ID tag system further comprises a first radiopaque MRI code section and a second radiopaque MM code section, wherein the first radiopaque MRI code section and the second radiopaque MRI code section face different radial directions relative to the central axis of the elongated housing.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 1A is a schematic illustration of a portion of the implantable medical device of FIG. 1;

FIG. 18 is a schematic view of a chevron that includes an ID tag formed therein;

Figure 1:
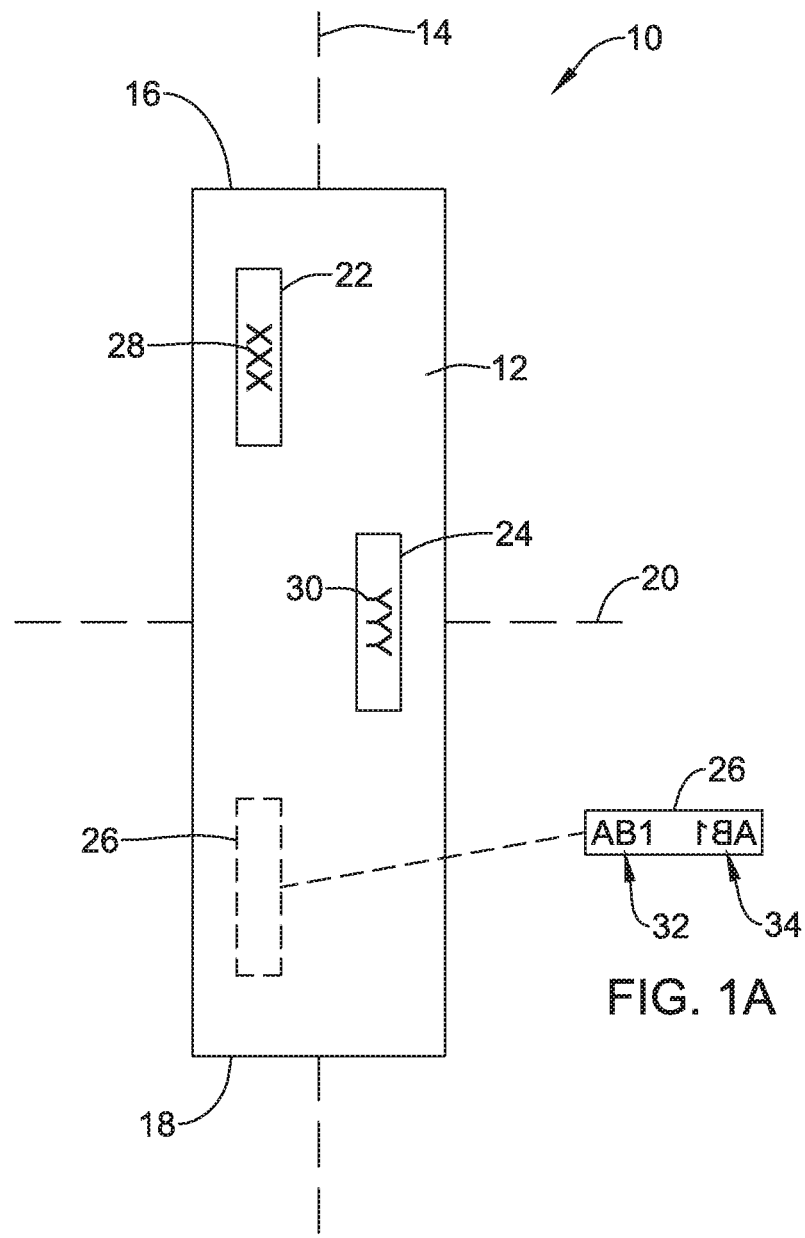
FIG. 1 is a schematic illustration of an implantable medical device in accordance with an illustrative embodiment of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 is a schematic illustration of an illustrative implantable medical device 10. The implantable medical device 10 may generically represent any variety of implantable medical devices, including but not limited to sensing devices, neurostimulators, pacing devices, defibrillation devices and the like. In some embodiments, the implantable medical device 10 may be a leaded or leadless pressure sensor, for example. While illustrated as having an elongated housing 12, it will be appreciated that the housing 12 may have other shapes, depending on where and how the implantable medical device 10 is delivered and deployed. For example, in some cases, the housing 12 may have a rectilinear shape, or may be generally cylindrical in shape. In some cases, the housing 12 may have a round or ovoid shape, depending on the application. In some cases, the implantable medical device 10 may be considered as having a longitudinal axis 14 extending lengthwise through the implantable medical device 10 from a first end 16 to a second 18. A radial axis 20 is shown perpendicular to the longitudinal axis 14.

In some instances, the implantable medical device 10 may include one or more ID tags that can be used to identify the implantable medical device 10 during imaging processes such as x-ray. As illustrated, the implantable medical device 10 includes a first ID tag 22, a second ID tag 24 and a third ID tag 26, shown in phantom as the third ID tag 26 is, in the illustrated orientation, on a back side of the implantable medical device 10. While three ID tags 22, 24, 26 are shown, in some cases there may be only one or two ID tags, or there may be four or more ID tags. While schematically illustrated on the housing 12, in some cases one or more of the ID tags 22, 24, 26, if present, may be located internally of the housing 12. If the first ID tag 22 is considered as being located at a first position, it can be seen that the second ID tag 24 is at a second position that is offset from the first position in at least one dimension. As illustrated, the second ID tag 24 is offset axially, along the direction of the longitudinal axis 14, as well as being offset radially, along the direction of the radial axis 20. As illustrated, the third ID tag 26 is at a third position that is offset both axially and radially from each of the first ID tag 22 and the second ID tag 24.

In some embodiments, the ID tags 22, 24, 26 may include a radiopaque identifier using a symbol and/or 1, 2 or 3 alphanumeric characters to identify a manufacturer and may include 1, 2, 3 or 4 alphanumeric characters to identify a model. The ID tags 22, 24, 26 may, for example, be used in a leadless pacemaker, a leadless pacemaker inside the heart, a dual chamber leadless pacemaker, an epicardial pacemaker, a leadless epicardial pacemaker or an implantable cardiac diagnostic device, among others. In some cases, a bar code such as a two dimensional bar code may be used. In some embodiments, the radiopaque identifier may include a two or four digit year identifier. In some cases, the radiopaque identifier may include a "B" to identify a company and a two digit model #, although this is merely illustrative.

The ID tags 22, 24, 26 are configured to be visible during imaging processes such as x-ray. With the implantable medical device 10, and thus the ID tags 22, 24 and 26, implanted within the body, the ID tags are configured to be visible and readable by an imaging process instituted from outside of the body. The imaging process may use x-rays, or any other suitable penetrating wave or particle such as neutron beams or gamma rays, as desired. In some cases, the ID tags 22, 24, 26, or portions thereof, are radiopaque. In some instances, the first ID tag 22 defines a first radiopaque manufacturer code section 28 that visually identifies a manufacturer of the implantable medical device 10, and the second ID tag 24 defines a second radiopaque manufacturer code section 30 that also visually identifies the manufacturer of the implantable medical device 10. In some cases, the first ID tag 22 and/or the second ID tag 24 may include a non-radiopaque substrate or carrier, and only the first radiopaque manufacturer code section 28 and/or the second radiopaque manufacturer code 30 is/are radiopaque. In some cases, the substrate or carrier forming the first ID tag 22 and/or the second ID tag 24 are radiopaque, and the first radiopaque manufacturer code section 28 and/or the second radiopaque manufacturer code section 30 represents an absence of radiopaque material. In some instances, the first ID tag 22 and/or the second ID tag 24 may be formed by printing alphanumeric characters or other identifying symbols onto a substrate or carrier using a radiopaque ink. In some cases, an ID tag 22, 24, 26 may be formed as a label or sticker that may be adhesively secured to a component within the implantable medical device 10. An ID tag 22, 24, 26 may, for example, include a high atomic weight foil. In some cases, an ID tag 22, 24, 26 may include a platinum foil that is enclosed in heat shrink tubing around an internal component such as a battery.

It will be appreciated that by including two or more radiopaque ID tags, arranged at offset positions, it may be easier to read at least one of the ID tags during an imaging process, especially for implantable medical devices that do not have a well-defined or fixed implanted orientation. While the first radiopaque manufacturer code section 28 is illustrated as "XXX" and the second radiopaque manufacturer code section 30 is illustrated as "YYY", it will be appreciated that this is illustrative only, as any variety of codes such as bar codes, alphanumeric characters, or any other suitable code or marking may be used, as desired.

In some embodiments, an ID tag may include a radiopaque manufacturer code as well as a mirror image of the radiopaque manufacturer code. FIG. 1A is an enlarged view of the third ID tag 26 showing a radiopaque manufacturer code 32 as well as a mirror image 34 of the radiopaque manufacturer code 32. As illustrated, the radiopaque manufacturer code reads "AB1", but this is of course illustrative only. Depending on the implanted orientation of the implantable medical device 10, the radiopaque manufacturer code 32 may be legible in an x-ray. In some cases, the mirror image 34 may be more legible. Accordingly, a single ID tag may provide the benefit of having two ID tags that are offset from each other. Regardless of whether an ID tag includes a code and a mirror image thereof, or if several ID tags are offset from each other, it will be appreciated that due to the nature of imaging processes such as x-ray, it is possible to see ID tags that are at various positions, both internal and external, relative to the housing 12.

Figure 2:
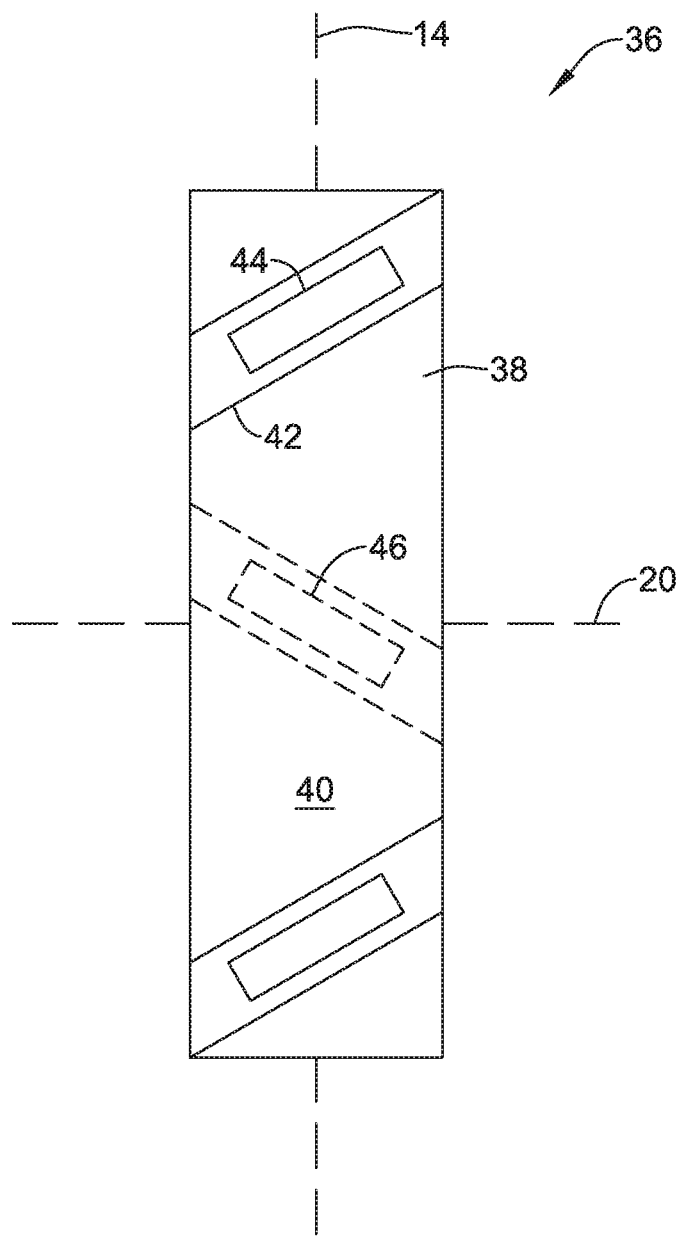
FIG. 2 is a schematic illustration of an implantable medical device in accordance with an illustrative embodiment of the present disclosure.

FIG. 2 provides a schematic illustration of an implantable medical device 36 having a longitudinal axis 14 and a radial axis 20. The implantable medical device 36 has a housing 38 with an outer surface 40. In the illustrated embodiment, a helix structure 42 wraps around the outer surface 40 of the housing 38. In other cases, the helix structure 42 may be internal to the housing 38. The illustrative helix structure 42 includes a first ID tag 44 and a second ID tag 46, similar to those discussed above with respect to FIG. 1.

As noted above, the implantable medical device 10 (FIG. 1) or the implantable medical device 36 (FIG. 2) may generally represent any number of different implantable devices. For illustrative purposes, the implantable medical device will be described with respect to a leadless cardiac pacemaker. Leadless cardiac pacemakers are often implanted within the heart and move with the heart as the heart beats. When so provided, the leadless cardiac pacemaker may not have a well-defined or fixed implanted orientation, at least relative to an imager such as an x-ray machine located outside of the body.

Figure 3:
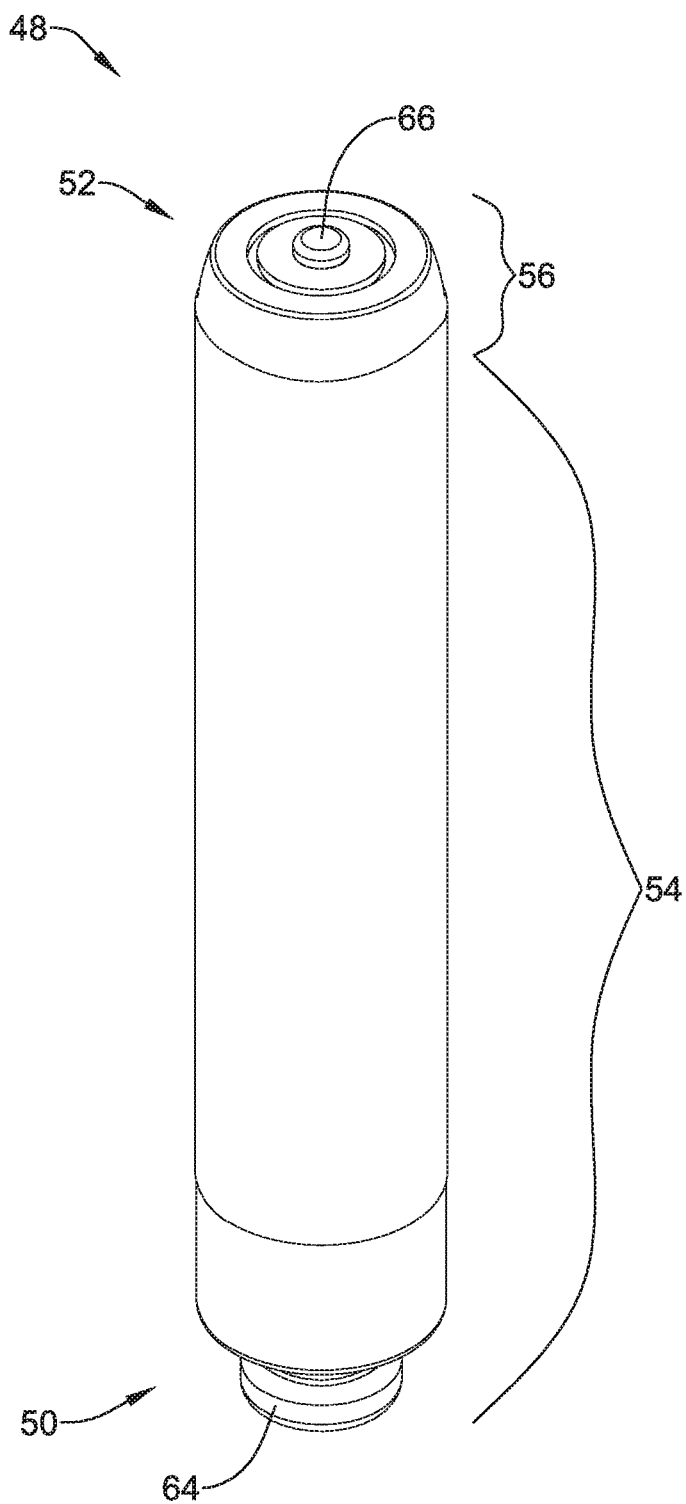
FIG. 3 is a perspective view of a leadless cardiac pacemaker in accordance with an illustrative embodiment of the present disclosure.

FIG. 3 provides a perspective view of an illustrative leadless cardiac pacemaker 48 extending from a proximal end 50 to a distal end 52. The leadless cardiac pacemaker 48 may be considered as including an energy storage section 54 and a circuit section 56. As will be discussed, the energy storage section 54 may house an energy source, such as a battery, for powering circuitry within the circuit section 56. While not illustrated, the leadless cardiac pacemaker 48 may include a fixation mechanism such as tines or a fixation helix.

Figure 4:
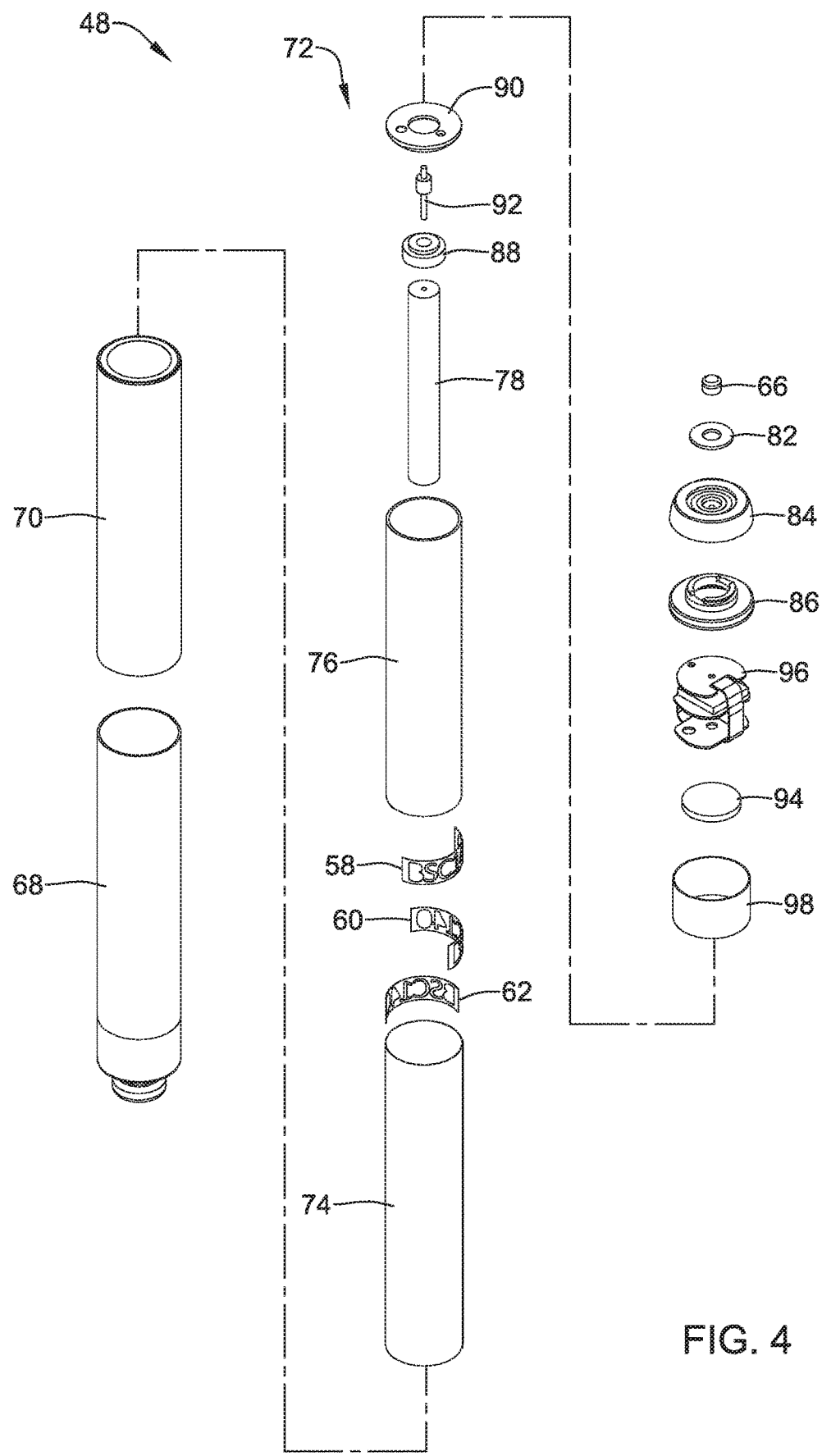
FIG. 4 is an exploded view of the illustrative leadless cardiac pacemaker of FIG. 3.

As seen in FIG. 3, the illustrative leadless cardiac pacemaker 48 includes a proximal end feature 64 that is located at the proximal end 50. In the example shown, the proximal end feature 64 is configured to permit grasping and removal of the leadless cardiac pacemaker 48 at some point during and/or subsequent to implantation. An electrode 66 is visible at the distal end 52 of the leadless cardiac pacemaker 48. FIG. 4 is an exploded view of the leadless cardiac pacemaker 48, showing some of the internal features of the leadless cardiac pacemaker 48, including various components that can be used to create or locate an ID tag.

Starting with the energy storage section 54, the illustrative leadless cardiac pacemaker 48 includes a housing 68 that includes the aforementioned proximal end feature 64. In some cases, as illustrated, an insulative coating 70 is disposed over at least a portion of the housing 68. The insulative coating 70 may be formed of parylene, but this is not required. The next several components form part of a battery 72. The illustrative battery 72 includes a battery liner 74, an anode 76 and a cathode 78. Several components pertain to the battery 72, including a battery feedthrough 88, a battery lid 90 and a battery pin 92. It will be appreciated that the battery 72 includes additional components and materials that, for simplicity, are not illustrated. The illustrative leadless cardiac pacemaker 48 includes a first ID tag 58, a second ID tag 60 and a third ID tag 62, each tag reading "BSC140" as an illustrative but non-limiting example. It can be seen that the second ID tag 60 is axially and radially offset from the first ID tag 58, and that the third ID tag 62 is axially and radially offset from the first ID tag 58 and the second ID tag 60. In the illustrated embodiment, the ID tags 58, 60 and 62 are located in or on the energy storage section 54 of the leadless cardiac pacemaker 48.

Moving to the circuit section 56, the illustrative leadless cardiac pacemaker 48 includes the electrode 66 and a drug collar 82 that is disposed proximate the electrode 66. An epoxy overmolding 84 sits under the drug collar 82. A ferrule 86 sits beneath the epoxy overmolding 84. A stacked printed circuit board 96 sits within a liner 98. As will be illustrated in subsequent Figures, a number of these components can be used or modified to carry or otherwise provide radiopaque ID tags such as those discussed with respect to FIGS. 1-3. FIGS. 5 through 13 provide illustrative but non-limiting examples of components that can be used or modified to carry or otherwise provide radiopaque ID tags. It will be appreciated that in these Figures, for simplicity, the ID tags are represented schematically and are intended to represent ID tags such as the first ID tag 22, including the first radiopaque manufacturer code section 28, and/or the second ID tag 24, including the second radiopaque manufacturer code section 30. While the ID tags in FIGS. 5-13 are schematically illustrated as having a particular orientation, this is not intended to be limiting in any fashion.

Figure 5:
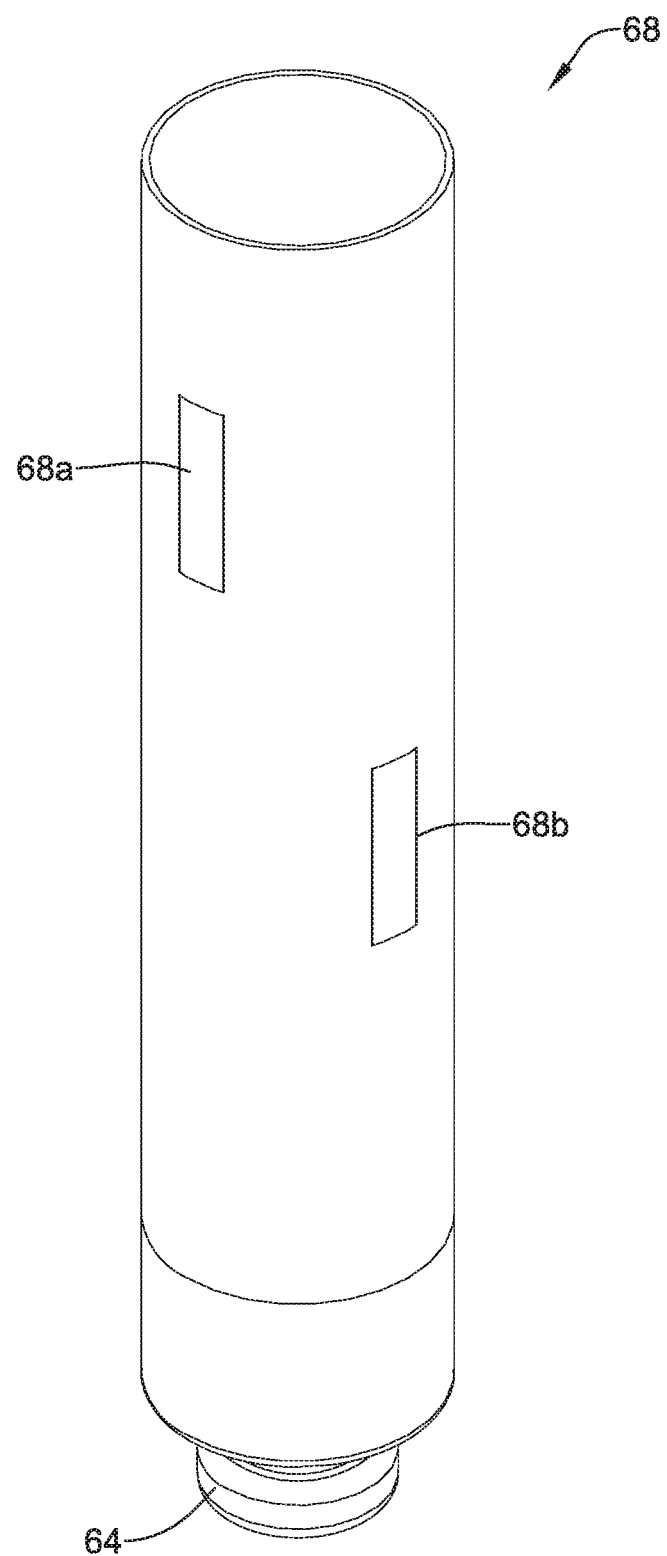
FIG. 5 is a perspective view of a housing useable as part of the illustrative leadless cardiac pacemaker of FIG. 3.

FIG. 5 illustrates the housing 68, schematically including a first ID tag 68a and a second ID tag 68b. Each of the first ID tag 68a and the second ID tag 68b include a radiopaque manufacturer code section that identifies the manufacturer of the leadless cardiac pacemaker 48 during an imaging process. The first ID tag 68a and the second ID tag 68b may each be formed in any desired manner, including but not limited to etching, machining, sputtering, cutting or sintering. In some embodiments, the first ID tag 68a and/or the second ID tag 68b may include a non-radiopaque substrate or carrier, with radiopaque characters or symbols providing the radiopaque manufacturer code information. In some instances, the substrate or carrier forming the first ID tag 68a and/or the second ID tag 68b are radiopaque, and the characters or symbols providing the manufacturer code information are either non-radiopaque or are cut out of the substrate or carrier. In some instances, the first ID tag 68a and/or the second ID tag 68b may be formed by printing alphanumeric characters or other identifying symbols onto a surface of the housing 68 using a radiopaque ink. These are just some examples. In some cases first ID tag 68a and/or the second ID tag 68b may be placed between the housing 68 and the insulative coating 70 when the insulative coating 70 is provided.

Figure 6:
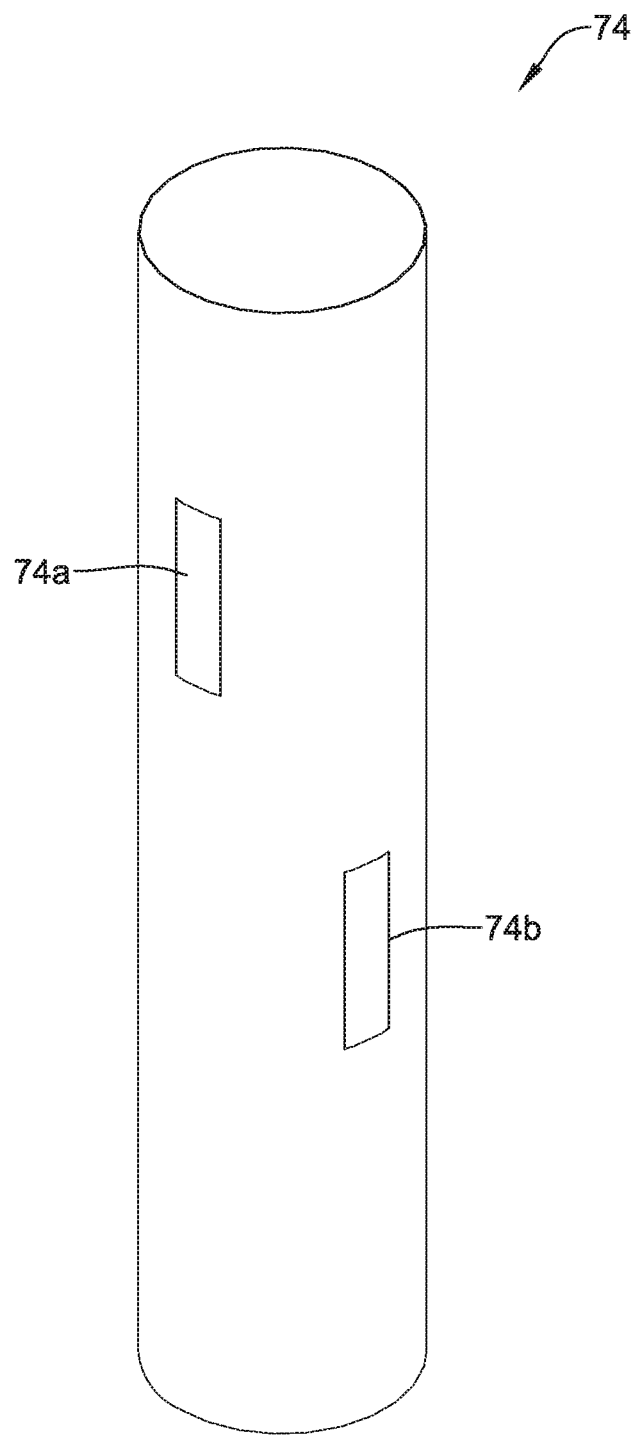
FIG. 6 is a perspective view of a battery liner useable as part of the illustrative leadless cardiac pacemaker of FIG. 3.

FIG. 6 illustrates the battery liner 74, schematically including a first ID tag 74a and a second ID tag 74b. Each of the first ID tag 74a and the second ID tag 74b include radiopaque manufacturer code sections that identify the manufacturer of the leadless cardiac pacemaker 48. The first ID tag 74a and the second ID tag 74b may each be formed in any desired manner, including but not limited to etching, machining, sputtering, cutting or sintering. In some embodiments, the first ID tag 74a and/or the second ID tag 74b may include a non-radiopaque substrate or carrier, with radiopaque characters or symbols providing the radiopaque manufacturer code information. In some instances, the substrate or carrier forming the first ID tag 74a and/or the second ID tag 74b are radiopaque, and the characters or symbols providing the manufacturer code information are either non-radiopaque or are cut out of the substrate or carrier. In some instances, the first ID tag 74a and/or the second ID tag 74b may be formed by printing alphanumeric characters or other identifying symbols onto a surface of the battery liner 74 using a radiopaque ink.

Figure 7:
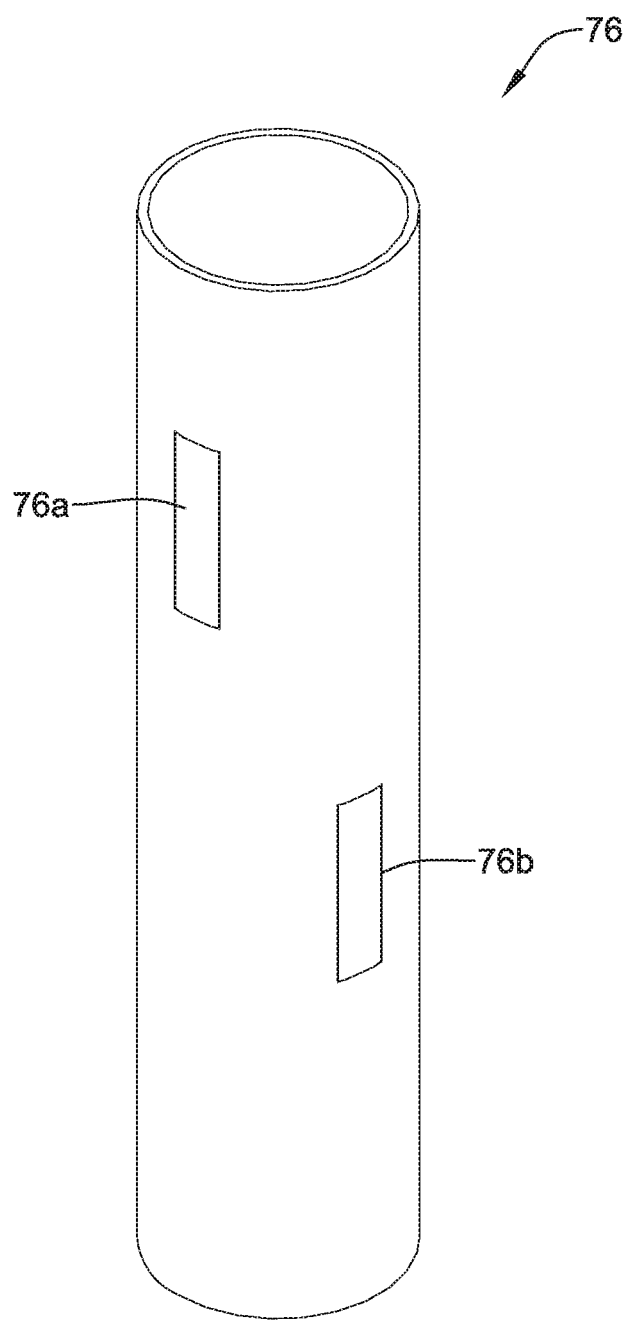
FIG. 7 is a perspective view of an anode useable as part of the illustrative leadless cardiac pacemaker of FIG. 3.

FIG. 7 illustrates the anode 76, schematically including a first ID tag 76a and a second ID tag 76b. Each of the first ID tag 76a and the second ID tag 76b include radiopaque manufacturer code sections that identify the manufacturer of the leadless cardiac pacemaker 48. The first ID tag 76a and the second ID tag 76b may each be formed in any desired manner, including but not limited to etching, machining, sputtering, cutting or sintering. In some embodiments, the first ID tag 76a and/or the second ID tag 76b may include a non-radiopaque substrate or carrier, with radiopaque characters or symbols providing the radiopaque manufacturer code information. In some instances, the substrate or carrier forming the first ID tag 76a and/or the second ID tag 76b are radiopaque, and the characters or symbols providing the manufacturer code information are either non-radiopaque or are cut out of the substrate or carrier. In some instances, the first ID tag 76a and/or the second ID tag 76b may be formed by printing alphanumeric characters or other identifying symbols onto a surface of the housing 68 using a radiopaque ink.

Figure 8:
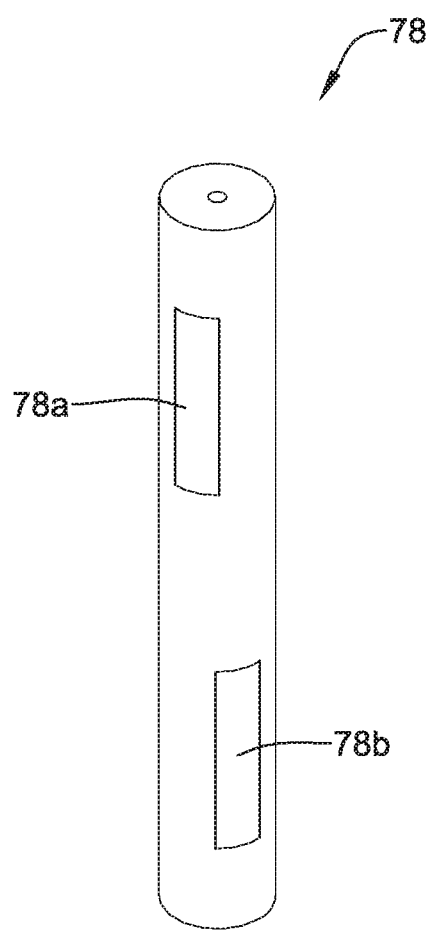
FIG. 8 is a perspective view of a cathode useable as part of the illustrative leadless cardiac pacemaker of FIG. 3.

FIG. 8 illustrates the cathode 78, schematically including a first ID tag 78a and a second ID tag 78b. Each of the first ID tag 78a and the second ID tag 78b include radiopaque manufacturer code sections that identify the manufacturer of the leadless cardiac pacemaker 48. The first ID tag 78a and the second ID tag 78b may each be formed in any desired manner, including but not limited to etching, machining, sputtering, cutting or sintering. In some embodiments, the first ID tag 78a and/or the second ID tag 78b may include a non-radiopaque substrate or carrier, with radiopaque characters or symbols providing the radiopaque manufacturer code information. In some instances, the substrate or carrier forming the first ID tag 78a and/or the second ID tag 78b are radiopaque, and the characters or symbols providing the manufacturer code information are either non-radiopaque or are cut out of the substrate or carrier. In some instances, the first ID tag 78a and/or the second ID tag 78b may be formed by printing alphanumeric characters or other identifying symbols onto a surface of the cathode 78 using a radiopaque ink.

Figure 9:
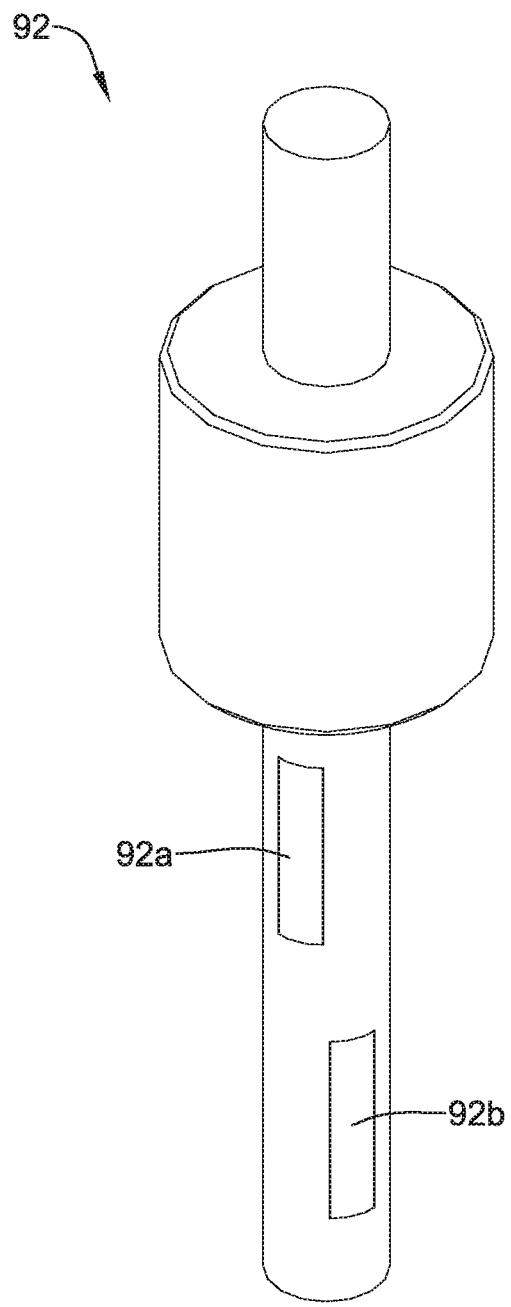
FIG. 9 is a perspective view of a battery pin useable as part of the illustrative leadless cardiac pacemaker of FIG. 3.

FIG. 9 illustrates the battery pin 92, schematically including a first ID tag 92a and a second ID tag 92b. Each of the first ID tag 92a and the second ID tag 92b include radiopaque manufacturer code sections that identify the manufacturer of the leadless cardiac pacemaker 48. The first ID tag 92a and the second ID tag 92b may each be formed in any desired manner, including but not limited to etching, machining, sputtering, cutting, or sintering. In some embodiments, the first ID tag 92a and/or the second ID tag 92b may include a non-radiopaque substrate or carrier, with radiopaque characters or symbols providing the radiopaque manufacturer code information. In some instances, the substrate or carrier forming the first ID tag 92a and/or the second ID tag 92b are radiopaque, and the characters or symbols providing the manufacturer code information are either non-radiopaque or are cut out of the substrate or carrier. In some instances, the first ID tag 92a and/or the second ID tag 92b may be formed by printing alphanumeric characters or other identifying symbols onto a surface of the battery pin 92 using a radiopaque ink.

Figure 10:
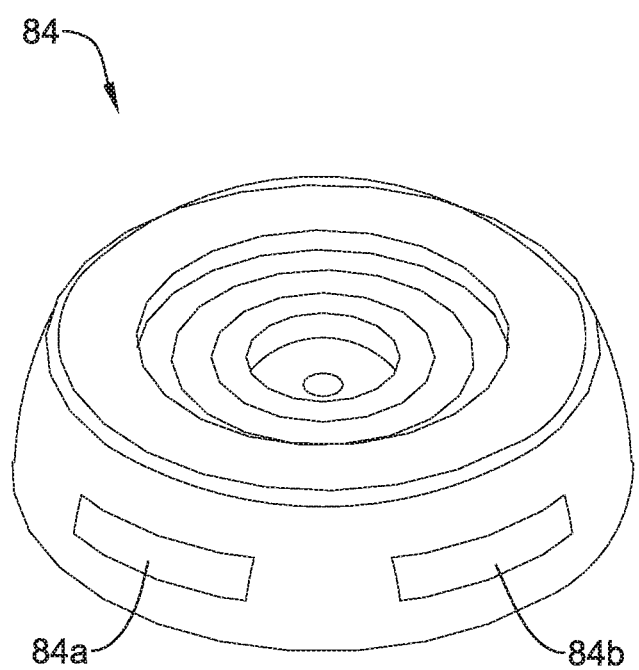
FIG. 10 is a perspective view of an overmolding useable as part of the illustrative leadless cardiac pacemaker of FIG. 3.

FIG. 10 illustrates the epoxy overmolding 84, schematically including a first ID tag 84a and a second ID tag 84b. Each of the first ID tag 84a and the second ID tag 84b include radiopaque manufacturer code sections that identify the manufacturer of the leadless cardiac pacemaker 48. The first ID tag 84a and the second ID tag 84b may each be formed in any desired manner, including but not limited to etching, machining, sputtering, cutting or sintering. In some embodiments, the first ID tag 84a and/or the second ID tag 84b may include a non-radiopaque substrate or carrier, with radiopaque characters or symbols providing the radiopaque manufacturer code information. In some instances, the substrate or carrier forming the first ID tag 84a and/or the second ID tag 84b are radiopaque, and the characters or symbols providing the manufacturer code information are either non-radiopaque or are cut out of the substrate or carrier. In some instances, the first ID tag 84a and/or the second ID tag 84b may be formed by printing alphanumeric characters or other identifying symbols onto a surface of the epoxy overmolding 84 using a radiopaque ink.

Figure 11:
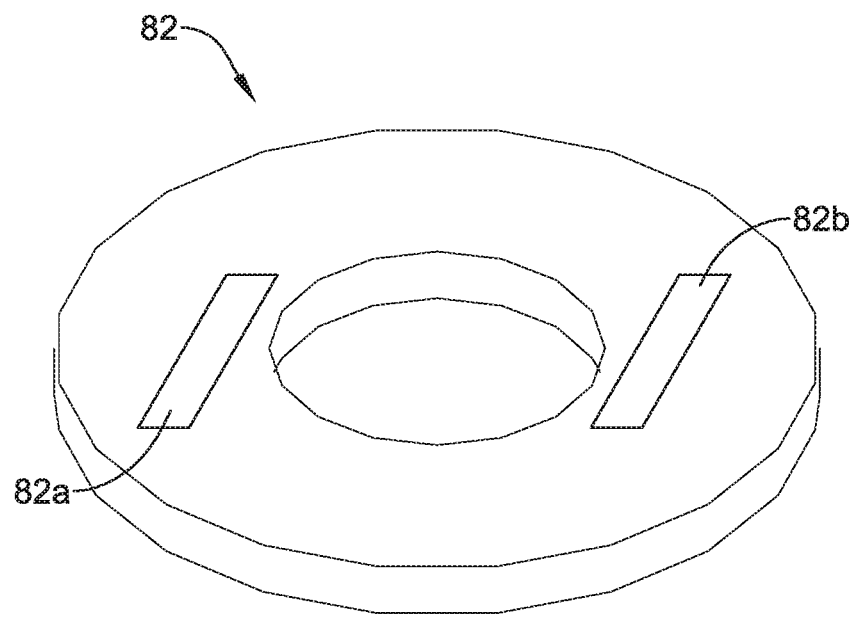
FIG. 11 is a perspective view of a drug collar useable as part of the illustrative leadless cardiac pacemaker of FIG. 3.

FIG. 11 illustrates the drug carrier 82, schematically including a first ID tag 82a and a second ID tag 82b. Each of the first ID tag 82a and the second ID tag 82b include radiopaque manufacturer code sections that identify the manufacturer of the leadless cardiac pacemaker 48. The first ID tag 82a and the second ID tag 82b may each be formed in any desired manner, including but not limited to etching, machining, sputtering, cutting or sintering. In some embodiments, the first ID tag 82a and/or the second ID tag 82b may include a non-radiopaque substrate or carrier, with radiopaque characters or symbols providing the radiopaque manufacturer code information. In some instances, the substrate or carrier forming the first ID tag 82a and/or the second ID tag 82b are radiopaque, and the characters or symbols providing the manufacturer code information are either non-radiopaque or are cut out of the substrate or carrier. In some instances, the first ID tag 82a and/or the second ID tag 82b may be formed by printing alphanumeric characters or other identifying symbols onto a surface of the drug collar 82 using a radiopaque ink.

Figure 12:
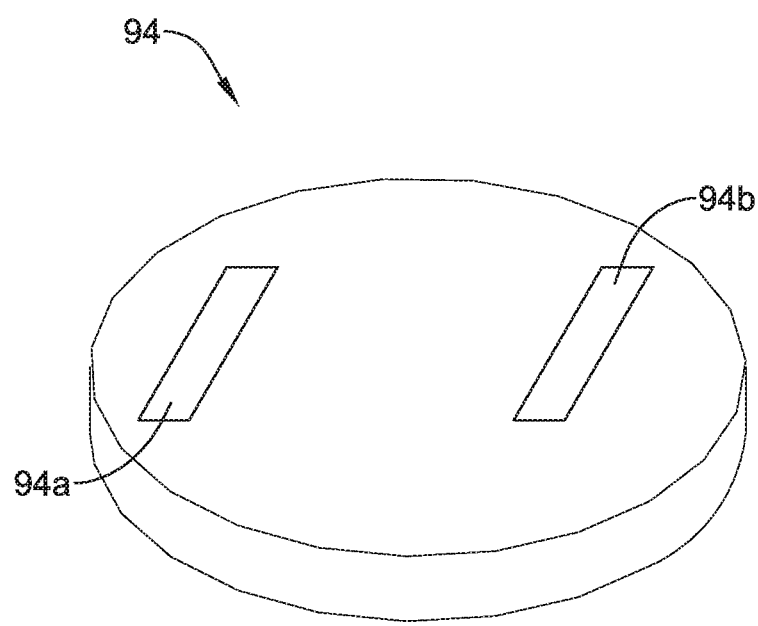
FIG. 12 is a perspective view of a desiccant useable as part of the illustrative leadless cardiac pacemaker of FIG. 3.

FIG. 12 illustrates the desiccant 94, schematically including a first ID tag 94a and a second ID tag 94b. Each of the first ID tag 94a and the second ID tag 94b include radiopaque manufacturer code sections that identify the manufacturer of the leadless cardiac pacemaker 48. The first ID tag 94a and the second ID tag 94b may each be formed in any desired manner, including but not limited to etching, machining, sputtering, cutting or sintering. In some embodiments, the first ID tag 94a and/or the second ID tag 94b may include a non-radiopaque substrate or carrier, with radiopaque characters or symbols providing the radiopaque manufacturer code information. In some instances, the substrate or carrier forming the first ID tag 94a and/or the second ID tag 94b are radiopaque, and the characters or symbols providing the manufacturer code information are either non-radiopaque or are cut out of the substrate or carrier. In some instances, the first ID tag 94a and/or the second ID tag 94b may be formed by printing alphanumeric characters or other identifying symbols onto a surface of the desiccant 94 using a radiopaque ink.

Figure 13:
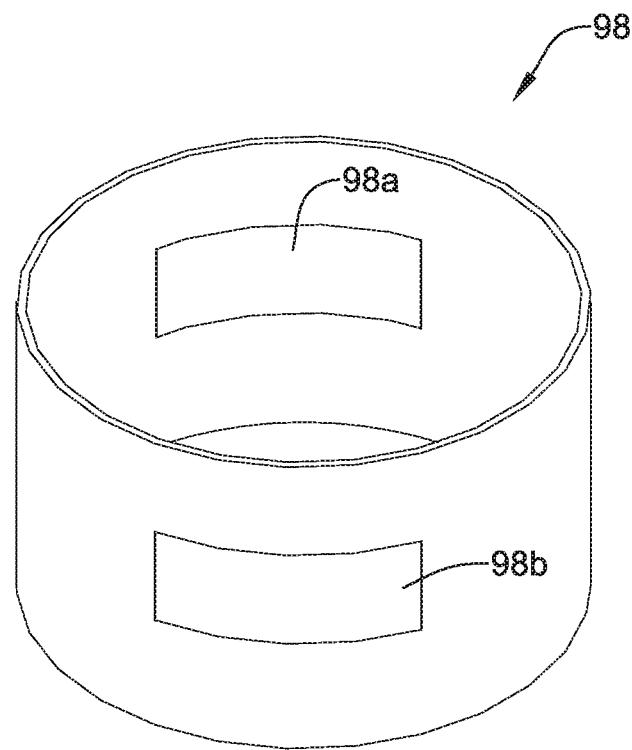
FIG. 13 is a perspective view of a liner useable as part of the illustrative leadless cardiac pacemaker of FIG. 3.

FIG. 13 illustrates the liner 98, schematically including a first ID tag 98a and a second ID tag 98b. Each of the first ID tag 98a and the second ID tag 98b include radiopaque manufacturer code sections that identify the manufacturer of the leadless cardiac pacemaker 48. The first ID tag 98a and the second ID tag 98b may each be formed in any desired manner, including but not limited to etching, machining, sputtering, cutting or sintering. In some embodiments, the first ID tag 98a and/or the second ID tag 98b may include a non-radiopaque substrate or carrier, with radiopaque characters or symbols providing the radiopaque manufacturer code information. In some instances, the substrate or carrier forming the first ID tag 98a and/or the second ID tag 98b are radiopaque, and the characters or symbols providing the manufacturer code information are either non-radiopaque or are cut out of the substrate or carrier. In some instances, the first ID tag 98a and/or the second ID tag 98b may be formed by printing alphanumeric characters or other identifying symbols onto a surface of the liner 98 using a radiopaque ink.

While each of FIGS. 5-13 illustrate each component part with both a first ID tag and a second ID tag, this is not required. In some cases, some component parts will not have any ID tags. In some cases, a particular component part may have one, two or more ID tags. In some cases, a first component part may have a first ID tag and a second component part may have a second ID tag. These are just examples.

Figure 14:
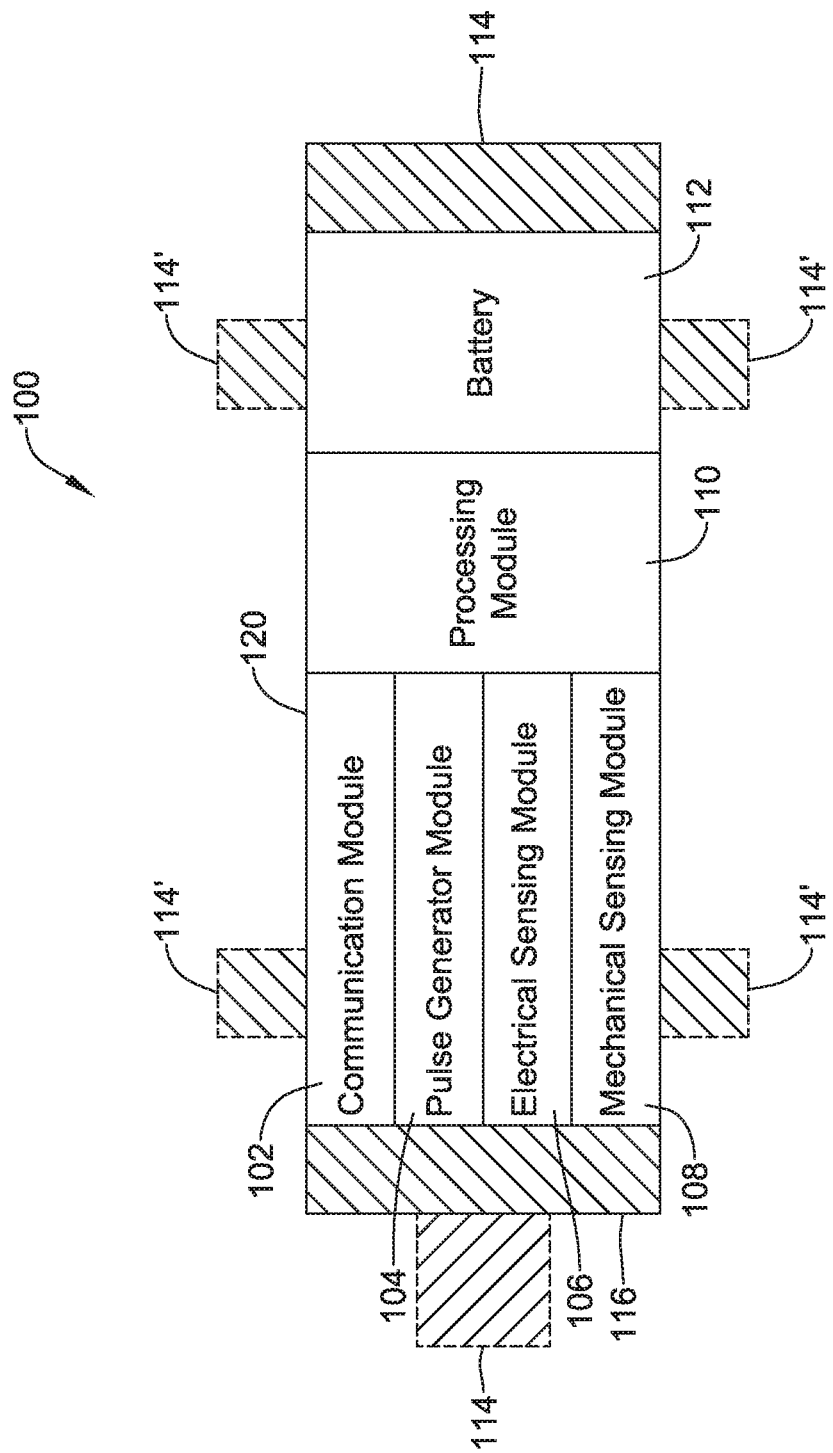
FIG. 14 is a schematic block diagram of the illustrative leadless cardiac pacemaker of FIG. 3.

FIG. 14 is a conceptual drawing of an exemplary leadless cardiac pacemaker 100 that may be implanted into a patient and may operate to sense physiological signals and parameters and deliver one or more types of electrical stimulation therapy to tissues of the patient. Example electrical stimulation therapy includes anti-tachycardia pacing (ATP) therapy, cardiac resynchronization therapy (CRT), bradycardia therapy, various types of pacing therapy including rate responsive pacing therapy, and/or the like. As can be seen in FIG. 14, LCP 100 may be a compact device with all components housed within LCP 100 or directly on housing 120. LCP 100 may include communication module 102, pulse generator module 104, electrical sensing module 106, mechanical sensing module 108, processing module 110, energy storage module 112, and electrodes 114.

As depicted in FIG. 14, LCP 100 may include electrodes 114, which can be secured relative to housing 120 but exposed to the tissue and/or blood surrounding LCP 100. Electrodes 114 may generally conduct electrical signals to and from LCP 100 and the surrounding tissue and/or blood. Such electrical signals can include communication pulses, electrical stimulation pulses, and intrinsic cardiac electrical signals. Intrinsic cardiac electrical signals may consist of the electrical signals generated by the heart and may be represented by an electrocardiogram (ECG). Electrodes 114 can be made up of one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In examples where electrodes 114 are secured directly to housing 120, electrodes 114 may have an insulative portion that electrically isolates electrodes 114 from adjacent electrodes, housing 120, and/or other portions of LCP 100. Some or all of electrodes 114 may be spaced from housing 120 and connected to housing 120 and/or other components of LCP 100 through connecting wires. In such embodiments, the electrodes 114 may be placed on a on a tail that extends from the housing 120. As shown in FIG. 14, in some examples, LCP 100 may additionally include electrodes 114'. Electrodes 114' are similar to electrodes 114 except that electrodes 114' are disposed on the sides of LCP 100 and increase the number of electrodes by which LCP 100 may deliver communication pulses and electrical stimulation pulses and/or sense for intrinsic cardiac electrical signals, communication pulses, and/or electrical stimulation pulses.

Electrodes 114 and/or 114' may have any of a variety of sizes and/or shapes, and may be spaced at any of a variety of distances. For example, electrodes 114 may have a diameter of two to twenty millimeters (mm). However, in other examples, electrodes 114 and/or 114' may have a diameter of two, three, five, seven millimeters (mm), or any other suitable diameter, dimension and shape. Example lengths for electrodes 114 and/or 114' include a length of zero, one, three, five, ten millimeters (mm), or any other suitable length. As used herein, the length is a dimension of electrodes 114 and/or 114' that extends outward from housing 120. Additionally, at least some of electrodes 114 and/or 114' may be spaced from one another by a distance of twenty, thirty, forty, fifty millimeters (mm), or any other suitable distance. The electrodes 114 and/or 114' of a single device may have different sizes with respect to each other, and the spacing of the electrodes on the device may not be uniform.

Communication module 102 may be electrically coupled to electrodes 114 and/or 114' and configured to deliver communication pulses to tissues of the patient for communicating with other devices such as sensors, programmers, other medical devices, and the like. Communication pulses, as used herein, may be any modulated signal that conveys information to another device, either by itself or in conjunction with one or more other modulated signals. In some examples, communication pulses are limited to only including sub-threshold signals which convey information. Other devices that communication module 102 may be configured to communicate with may be located either external or internal to the patient's body. Communication module 102 may additionally be configured to sense for communication pulses delivered by the other devices, which are located externally to LCP 100. Irrespective of the location, LCP and the other devices may communicate with each other via communication module 102 to accomplish one or more desired functions. Some example functions include storing communicated data, using communicated data for determining occurrences of arrhythmias, coordinating delivery of electrical stimulation therapy, and/or other functions.

LCP 100 and the other devices may use the delivered communication pulses to communicate raw information, processed information, messages, and/or other data. Raw information may include information such as sensed electrical signals (e.g. a sensed ECG), signals gathered from coupled sensors, and the like. In some examples, the raw information may include signals that have been filtered using one or more signal processing techniques. Processed information may include any information that has been determined by LCP 100. For example, processed information may include a determined heart rate, timings of determined heartbeats, timings of other determined events, determinations of threshold crossings, expirations of monitored time periods, and determined parameters such as activity parameters, blood-oxygen parameters, blood pressure parameters, heart sound parameters, and the like. Messages may include instructions directing another device to take action, notifications of imminent actions of the sending device, requests for reading from the receiving device or writing data to the receiving device.

In at least some examples, communication module 102 (or LCP 100) may further include switching circuitry to selectively connect one or more of electrodes 114 and/or 114' to communication module 102 in order to select via which electrodes 114 and/or 114' communication module 102 delivers the communication pulses. Additionally, communication module 102 may be configured to use one or more methods for communicating with other devices. For example, communication module 102 may communicate via conducted signals, radiofrequency (RF) signals, optical signals, acoustic signals, inductive coupling, and/or any other signals or methods suitable for communication.

Pulse generator module 104 of LCP 100 may also be electrically connected to one or more of electrodes 114 and/or 114'. Pulse generator module 104 may be configured to generate electrical stimulation pulses and deliver the electrical stimulation pulses to tissues of a patient via electrodes 114 and/or 114' electrodes in order to effectuate one or more electrical stimulation therapies. Electrical stimulation pulses as used herein are meant to encompass any electrical signals that may be delivered to tissue of a patient for purposes of treatment of any type of disease or abnormality. When used to treat heart diseases or abnormalities, the electrical stimulation pulses may generally be configured so as to capture the heart of the patient—cause the heart to contract in response to the delivered electrical stimulation pulse. In at least examples where pulse generator 104 is configured to generate specific types of electrical stimulation pulses termed defibrillation/cardioversion pulses, pulse generator module 104 may include one or more capacitor elements.

Pulse generator module 104 may include capability to modify the electrical stimulation pulses, such as by adjusting a pulse width or amplitude of the electrical stimulation pulses, in order to ensure that the delivered electrical stimulation pulses consistently capture the heart. Pulse generator module 104 may use energy stored in energy storage module 112 to generate the electrical stimulation pulses. In at least some examples, pulse generator module 104 (or LCP 100) may further include switching circuitry to selectively connect one or more of electrodes 114 and/or 114' to pulse generator module 104 in order to select via which electrodes 114 and/or 114' pulse generator 104 delivers the electrical stimulation pulses.

In some examples, LCP 100 may include electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114'. In some examples, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be further connected to processing module 110 and may provide signals representative of the sensed cardiac electrical signals and/or physiological signals to processing module 110. Although described with respect to FIG. 1 as separate sensing modules, in some examples, electrical sensing module 106 and mechanical sensing module 108 may be combined into a single module.

Processing module 110 may be configured to control the operation of LCP 100. For example, processing module 110 may be configured to receive cardiac electrical signals from electrical sensing module 106 and/or physiological signals from mechanical sensing module 108. Based on the received signals, processing module 110 may determine occurrences and types of arrhythmias. Processing module 110 may further receive information from communication module 102. In some examples, processing module 110 may additionally use such received information to determine occurrences and types of arrhythmias. However, in other examples, LCP 100 may use the received information instead of the signals received from electrical sensing module 106 and/or mechanical sensing module 108—for instance if the received information is more accurate than the signals received from electrical sensing module 106 and/or mechanical sensing module 108 or if electrical sensing module 106 and/or mechanical sensing module 108 have been disabled or omitted from LCP 100.

Based on any determined arrhythmias, processing module 110 may then control pulse generator module 104 to generate electrical stimulation pulses in accordance with one or more electrical stimulation therapies to treat the determined arrhythmias. For example, processing module 110 may control pulse generator module 104 to generate pacing pulses with varying parameters and in different sequences to effectuate one or more electrical stimulation therapies. In controlling pulse generator module 104 to deliver bradycardia pacing therapy, processing module 110 may control pulse generator module 104 to deliver pacing pulses designed to capture the heart of the patient at a regular interval to prevent the heart of a patient from falling below a predetermined threshold. For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Processing module 110 may then control pulse generator module 104 to reduce the rate of delivered pacing pulses down to a safe level. In CRT, processing module 110 may control pulse generator module 104 to deliver pacing pulses in coordination with another device to cause the heart to contract more efficiently. Additionally, in cases where pulse generator module 104 is capable of generating defibrillation and/or cardioversion pulses for defibrillation/cardioversion therapy, processing module 110 may control pulse generator module 104 to generate such defibrillation and/or cardioversion pulses. In other examples, processing module 110 may control pulse generator module 104 to generate electrical stimulation pulses to provide electrical stimulation therapies different than those described herein to treat one or more detected cardiac arrhythmias.

Aside from controlling pulse generator module 104 to generate different types of electrical stimulation pulses and in different sequences, in some examples, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may ensure that LCP 100 is able to provide effective delivery of electrical stimulation therapy.

In some examples, processing module 110 may further control communication module 102 to send information to other devices. For example, processing module 110 may control communication module 102 to generate one or more communication pulses for communicating with other devices of a system of devices. For instance, processing module 110 may control communication module 102 to generate communication pulses in particular sequences, where the specific sequences convey different data to other devices. Communication module 102 may also conduct any received communication signals to processing module 110 for potential action by processing module 110.

In further examples, processing module 110 may additionally control switching circuitry by which communication module 102 and pulse generator module 104 deliver communication pulses and electrical stimulation pulses to tissue of the patient. As described above, both communication module 102 and pulse generator module 104 may include circuitry for connecting one or more electrodes 114 and/114' to communication module 102 and pulse generator module 104 so those modules may deliver the communication pulses and electrical stimulation pulses to tissue of the patient. The specific combination of one or more electrodes by which communication module 102 and pulse generator module 104 deliver communication pulses and electrical stimulation pulses influence the reception of communication pulses and/or the effectiveness of electrical stimulation pulses. Although it was described that each of communication module 102 and pulse generator module 104 may include switching circuitry, in some examples LCP 100 may have a single switching module connected to all of communication module 102, pulse generator module 104, and electrodes 114 and/or 114'. In such examples, processing module 110 may control the single switching module to connect modules 102/104 and electrodes 114/114'.

In still additional examples, processing module 110 may control pulse generator module 104 to generate the communication pulses for communicating with external devices. In such examples, communication module 102 may not include the capability to generate communication pulses. In some even additional examples, electrical sensing module 106 may further include the capability to sense communication pulses. In such examples, electrical sensing module 106 may communicate any received communication pulses to processing module 110. In such examples, LCP 100 may not include communication module 102, as the functions of communication module 102 are subsumed within pulse generator module 104 and electrical sensing module 106. However, in such examples, LCP 100 may not be able to simultaneously generate both communication pulses and electrical stimulation pulses.

In some examples, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby increasing the battery life of LCP 100. In other examples, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional examples, may further include a memory circuit and processing module 110 may store information on and read information from the memory circuit. In other examples, LCP 100 may include a separate memory circuit (not shown) that is in communication with processing module 110, such that processing module 110 may read and write information to and from the separate memory circuit. The memory circuit, whether part of processing module 110 or separate from processing module 110 may have address lengths of, for example, eight bits. However, in other examples, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

Energy storage module 112 may provide a power source to LCP 100 for its operations. In some examples, energy storage module 112 may be a non-rechargeable lithium-based battery. In other examples, the non-rechargeable battery may be made from other suitable materials known in the art. Because LCP 100 is an implantable device, access to LCP 100 may be limited. In such circumstances, it is necessary to have sufficient energy capacity to deliver therapy over an extended period of treatment such as days, weeks, months, or years. In some examples, energy storage module 112 may a rechargeable battery in order to facilitate increasing the useable lifespan of LCP 100. In still other examples, energy storage module 112 may be other types of energy storage devices such as capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix anchor 116 within the cardiac tissue. In other examples, anchor 116 may include other structures such as barbs, spikes, or the like to facilitate engagement with the surrounding cardiac tissue.

Figure 15:
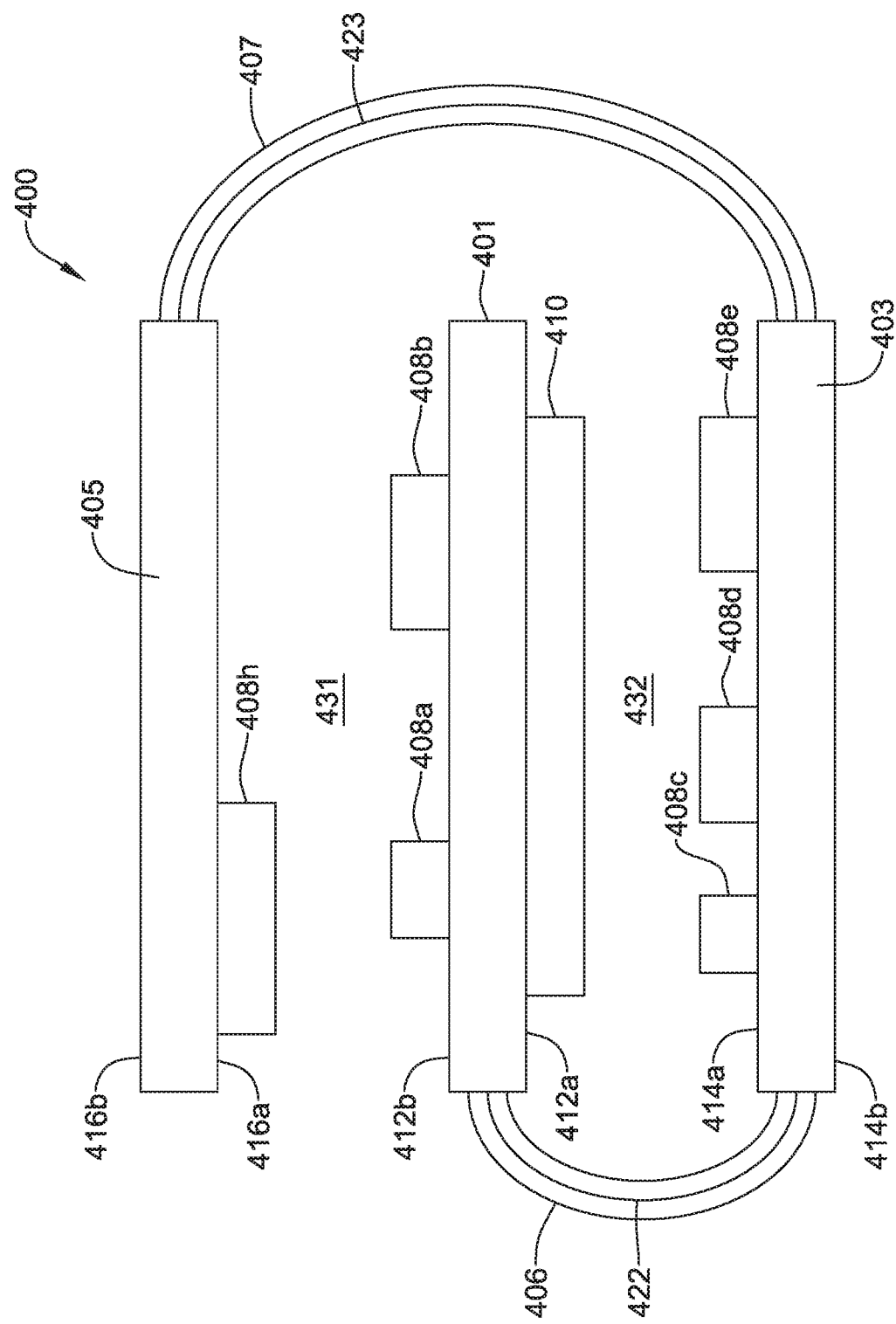
FIG. 15 is a schematic illustration of an example electrical circuit useable as part of the illustrative leadless cardiac pacemaker of FIG. 3.

The modules shown in FIG. 14 may be manifested in circuitry that is disposed within the circuit section 56 (FIG. 3). FIG. 15 provides an illustrative but non-limiting example of the stacked printed circuit board 96 (FIG. 4). In the example of FIG. 15, example circuit 400 has three separate island sections including first island section 401, second island section 403, and third island section 405. Island sections 401, 403, and 405 are shown separated by first ribbon section 406 and second ribbon section 407. Each of island sections 401, 403, and 405 may include first major opposing surfaces 412A, 414A, and 416A and second major opposing surfaces 412B, 414B, and 416B. Second island section 403 and third island section 405 may also include feedthroughs (not visible) that may be electrically connected to electrodes 114/114', an electrical common reference, and/or an energy storage device.

In some examples, each island section may be circular in shape, but this is not required. In some cases, each island section has a diameter that is less than an inner diameter of a cross section of an implantable medical device housing (such as LCP 100) so that the circuit 400 may fit once folded into a stacked configuration. Example diameters range from 3.8 to 12.7 millimeters (mm). The island sections may be triangular, square, ovoid or any other desired shape. In some cases, the flexible ribbon sections may range from 3.8 to 12.7 mm.

Processing module 410 and circuit elements 408A-H may be examples of circuit elements that may implement the functions of communication module 102, pulse generator module 104, electrical sensing module 106, mechanical sensing module 108, and/or processing module 110. Processing module 410 may include any of the circuit elements or components described with respect to processing module 110, such as a pre-programmed logic chip or a programmable microprocessor. Circuit elements 408A-H may represent capacitors, resistors, diodes, ASICS, and/or any other suitable circuit elements or components.

In some examples, at least one island section may have one or more components affixed to both major opposing surfaces of that island section. In the specific example of FIG. 15, island section 401 includes processing module 410 affixed to first major opposing surface 412A and circuit elements 408A-B (shown in dashed) on second major opposing surface 412B. In examples where island sections 401, 403, and 405 include PCBs, the PCBs may include conductive traces that electrically connect processing module 410 and circuit elements 408A-H to produce the desired circuit functionality. Alternatively, in examples where circuit 400 includes one common substrate, any processing module 410 and/or circuit element 408A-H connected to an island section may be connected to one or more internal conductive trace layers, thereby electrically connecting the processing module 410 and/or the various circuit elements 408A-H to produce the desired circuit functionality.

Ribbon sections 406, 407 may include traces, such as trace 422 in first ribbon section 406 and trace 423 in second ribbon section 407. Traces 422, 423 may be conductive and thereby electrically connect certain components on island sections 401, 403, and 405. First and second ribbon sections 406, 407 may be relatively more flexible than island sections 401, 403, and 405. For example, first and second ribbon sections 406, 407 may be made from a flexible substrate, such as a polymer, with traces 422, 423 embedded within the flexible substrate while island sections 401, 403, and 405 include more rigid PCBs. Alternatively, where island sections 401, 403, and 405 and first and second ribbon sections 406, 407 share a common substrate, first and second ribbon sections 406, 407 may be relatively thinner than island sections 401, 403, and 405.

Additionally, in at least some examples, first ribbon section 406 and second ribbon section 407 may have differing lengths. As depicted in FIG. 15, first ribbon section 406 has a shorter length than second ribbon section 407, however, in other examples, the lengths may be reversed and, of course, the lengths may be the same. Island sections 401, 403, and 405 are stacked with first major opposing surfaces 412A and 414A of island sections 401 and 403 facing each other and with second major opposing surface of island section 401 and first major opposing surface 416A facing each other, thereby creating spaces 431 and 432 between island sections 405, 401 and island sections 401, 403, respectively.

In some embodiments, the island sections 401, 402, 403 may include rigid printed circuit boards, with metal or other traces electrically connecting each of the components on each of the island sections 401, 402, 403. Ribbon sections 406, 407 may include a flexible substrate, such as a polymer including a polyimide. Traces may be embedded within the ribbon sections 406, 407 to provide electrical communication therethrough. In some cases, a common substrate may instead extend through the island sections 401, 402, 403 and through the ribbon sections 406, 407. The island sections 401, 402, 403 may include a multi-layered substrate that includes alternating conductive substrates and non-conductive substrates while the ribbon sections 406, 407 are thinner and thus more flexible. In at least some examples, the conductive substrate may be metal, or other suitable conductive material, and the non-conductive substrate may be a type of polymer, such as a polyamide or other suitable non-conductive material. Further details regarding the construction of the circuit 400 may be found in U.S. Provisional Application No. 62/086,015 filed Dec. 1, 2014, which application is incorporated by reference herein in its entirety.

In some examples, a filler material may be disposed within spaces 431 and 432 in order isolate processing module 410 and circuit elements 408A-H disposed on different island sections. In at least some examples, the filler material may be formed such that when the filler material is disposed within spaces 431 and/or 432, the filler material folds around the processing module 410 and/or circuit elements 408A-H to isolate even the components on the same island section. In some examples, the isolation that the filler material provides may be electrical isolation. For instance, the filler material may prevent the components on islands 401, 403, and/or 405 from contacting each other and causing a short circuit. In other examples, the filler material may instead, or additionally, provide mechanical isolation between the components of islands 401, 403, and/or 405. For instance, the device housing islands 401, 403, and/or 405 may be subjected to motion, and the filler material may prevent the components of islands 401, 403, and/or 405 from striking each other and causing damage. In at least some examples, the filler material may be a desiccant. Some example filler materials include silicone or other inert compounds.

Figure 16:
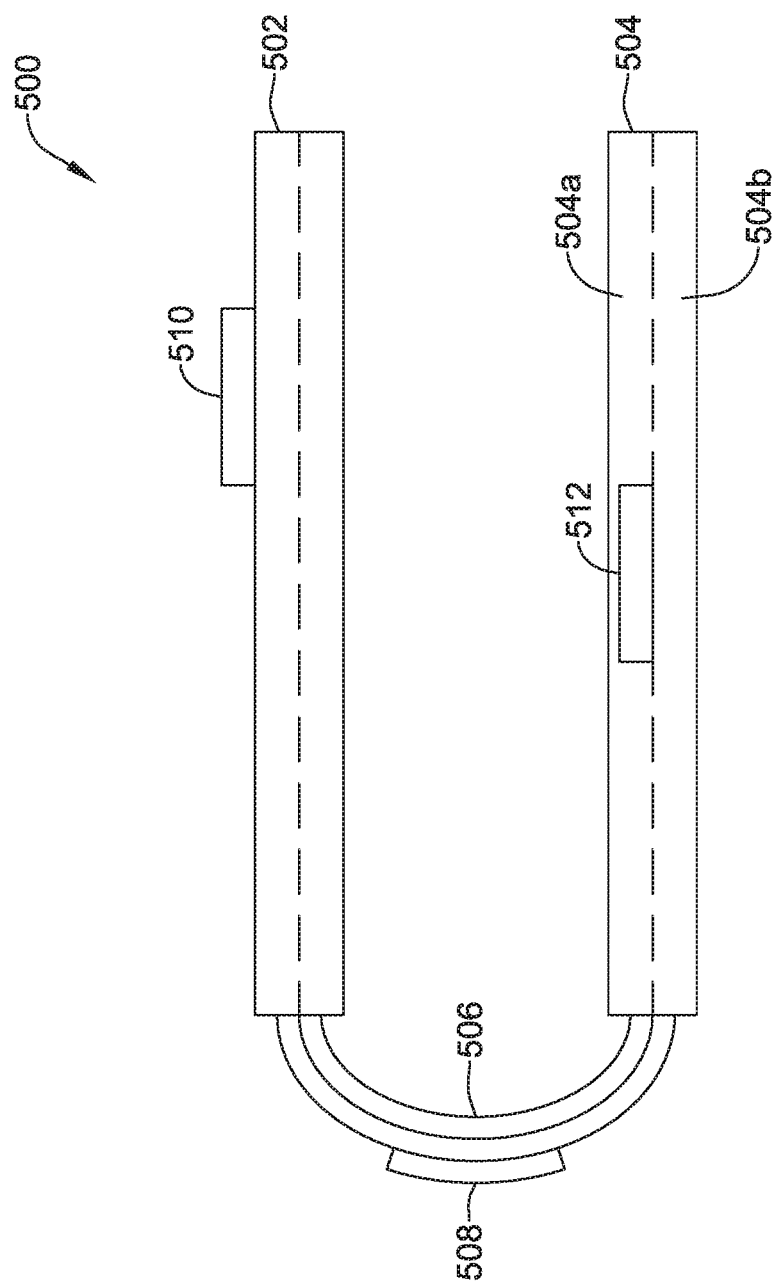
FIG. 16 is a schematic illustration of an example electrical circuit, including an ID tag, in accordance with an example of the present disclosure.

FIG. 16 provides a genericized view of a circuit such as circuit 400 (FIG. 15), but provides additional details regarding the possible inclusion of one or more ID tags. In FIG. 15, a circuit 500 includes a first island section 502 and a second island section 504, operably coupled together via a flexible ribbon section 506. While two island sections 502, 504 are illustrated, it will be appreciated that in other embodiments the circuit 500 may include only a single island section or may include three or more island sections. In some embodiments, an ID tag 508 may be secured relative to the flexible ribbon section 506. The ID tag 508 may be printed directly onto the flexible ribbon section 506 using radiopaque ink, for example. In some instances, the ID tag 508 may be separately formed on a substrate or carrier that is subsequently attached to the flexible ribbon section 506. While a single ID tag 508 is illustrated on the flexible ribbon section 506, in some instances there may be multiple ID tags, or a single ID tag 508 may include manufacture identification information portrayed twice, once in mirror fashion.

In some embodiments, the island sections 502, 504 may include one or more ID tags. For example, in some cases, an ID tag 510 may be printed or otherwise formed on an outer surface of an island section such as the island section 502. In some cases, an island section such as the island section 504 may include several layers 504a and 504b, for example, and an ID tag 512 may be disposed between the layers 504a and 504b. In some cases, an ID tag may be disposed on the back of the ASIC and/or adhesively secured to any of the electronic components present in the circuit 400 (FIG. 15).

Figure 17A:
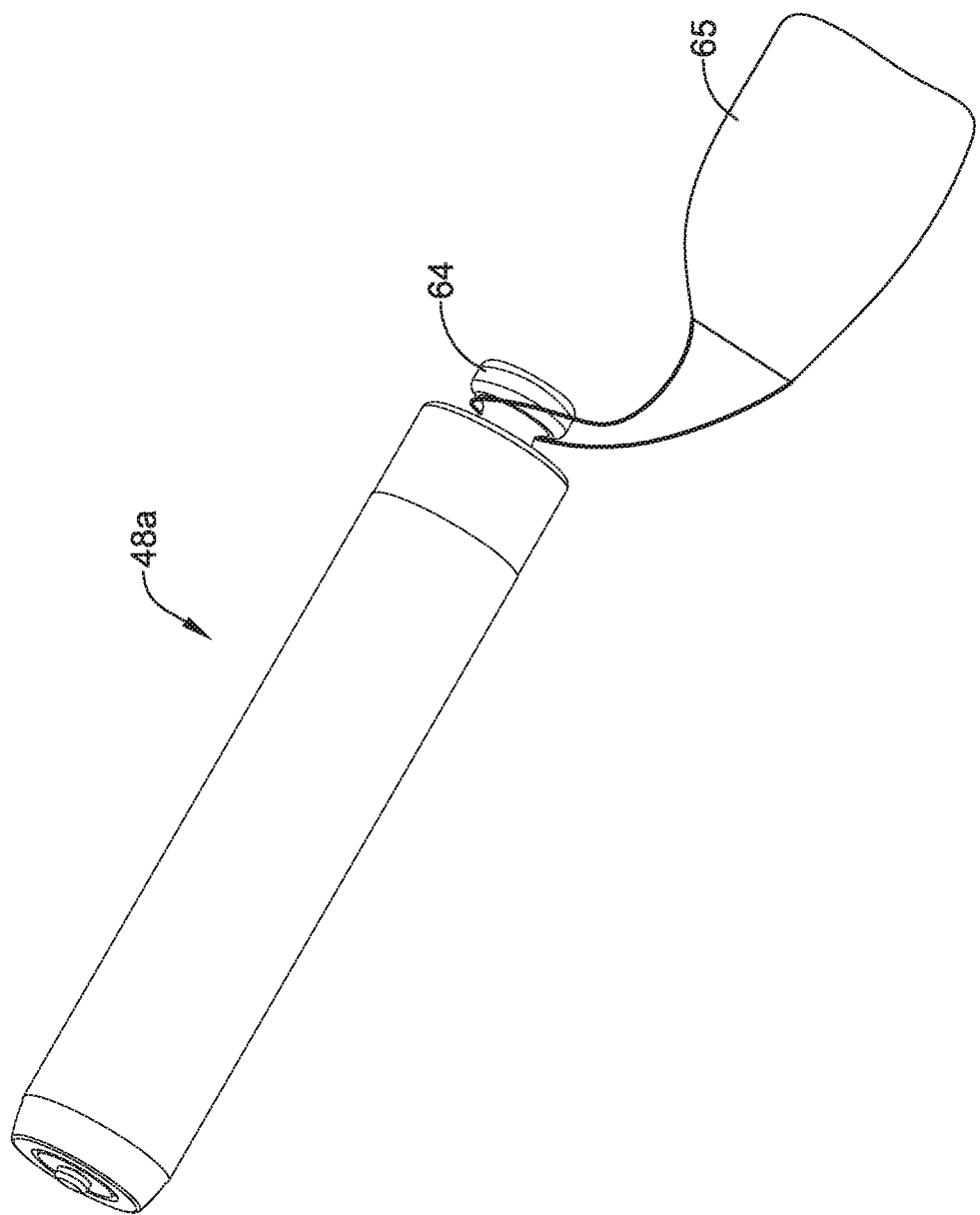
FIG. 17A is a perspective view of a illustrative leadless cardiac pacemaker, which includes an ID tag secured relative to a proximal end feature.

FIG. 17A is a view of an illustrative leadless cardiac pacemaker 48a, including a proximal end feature 64a that enables the leadless cardiac pacemaker 48a to be grasped during initial delivery and deployment and/or during subsequent removal. In some cases, as illustrated, an ID tag 65 may be crimped or otherwise secured to the proximal end feature 64a in order to provide identifying information during an imaging process such as x-ray. While the ID tag 65 is shown schematically, it will be appreciated that the ID tag 65 may include a radiopaque manufacturer code section, and may optionally also include a mirror image thereof. In some cases, the ID tag 65 may be inside or embedded in the proximal end feature 64a.

Figure 17B:
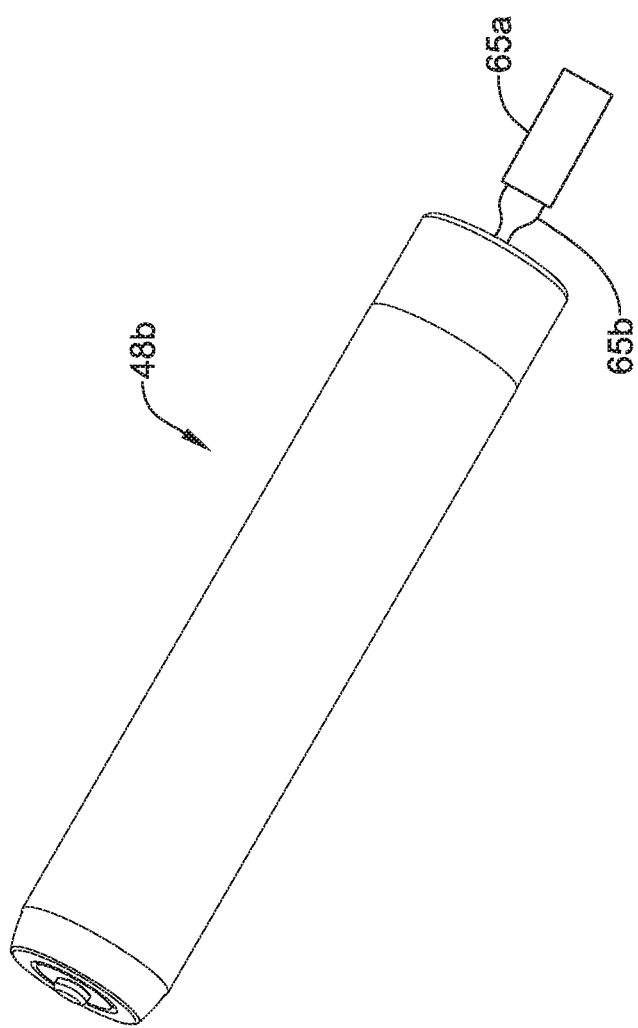
FIG. 17B is a perspective view of an illustrative leadless cardiac pacemaker, which includes an ID tag forming a proximal end feature.

FIG. 17B is a view of an illustrative leadless cardiac pacemaker 48b, including an ID tag 65a that is secured to the leadless cardiac pacemaker 48b via one or more (two are illustrated) cables 65b, or other flexible or rigid attachment mechanisms. While the ID tag 65a is shown schematically, it will be appreciated that the ID tag 65a may include a radiopaque manufacturer code section, and may optionally also include a mirror image thereof. In some cases, the leadless cardiac pacemaker 48b may be retrieved by grabbing the ID tag 65a with a snare or similar tool.

FIG. 18 is a schematic view of a chevron 200 that may be used within an implantable medical device such as the implantable medical device 10 in order to provide an indication during delivery as to whether the implantable medical device 10 is twisting or otherwise moving/rotating. The illustrative chevron 200 is formed of a radiopaque material. In some instances, as illustrated, a first ID tag 202a and a second ID tag 202b may be formed by cutting, etching or otherwise removing radiopaque material to form characters 204a and 204b. When so provided, the characters 204a and 204b will show up in an x-ray as relatively darker than the rest of the radiopaque chevron 200.

Figure 19:
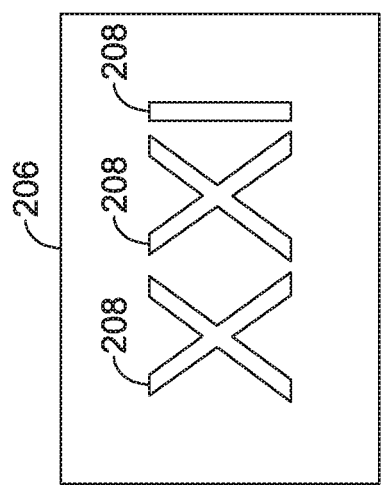
FIGS. 19 and 20 illustrate a method of forming a radiopaque ID tag in accordance with an example of the present disclosure.
Figure 20:
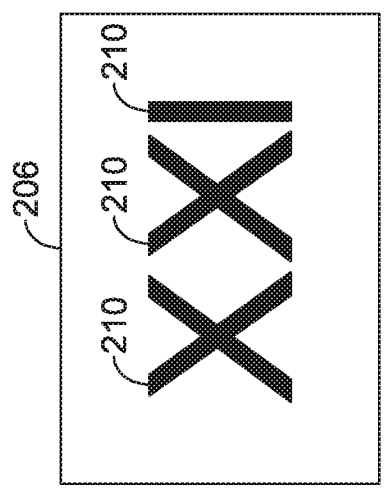

In some embodiments, a radiopaque ID tag may be formed by first etching alphanumeric characters or other symbols into a substrate, then filling the etching with a radiopaque material. FIGS. 19 and 20 illustrate an embodiment in which characters 208 are outlined on a substrate 206 by etching out the shape of the characters 208. A radiopaque material 210 is placed within the etched shapes to provide radiopaque characters. In some instances, a platinum wire may be used to provide the radiopaque material.

Figure 21:
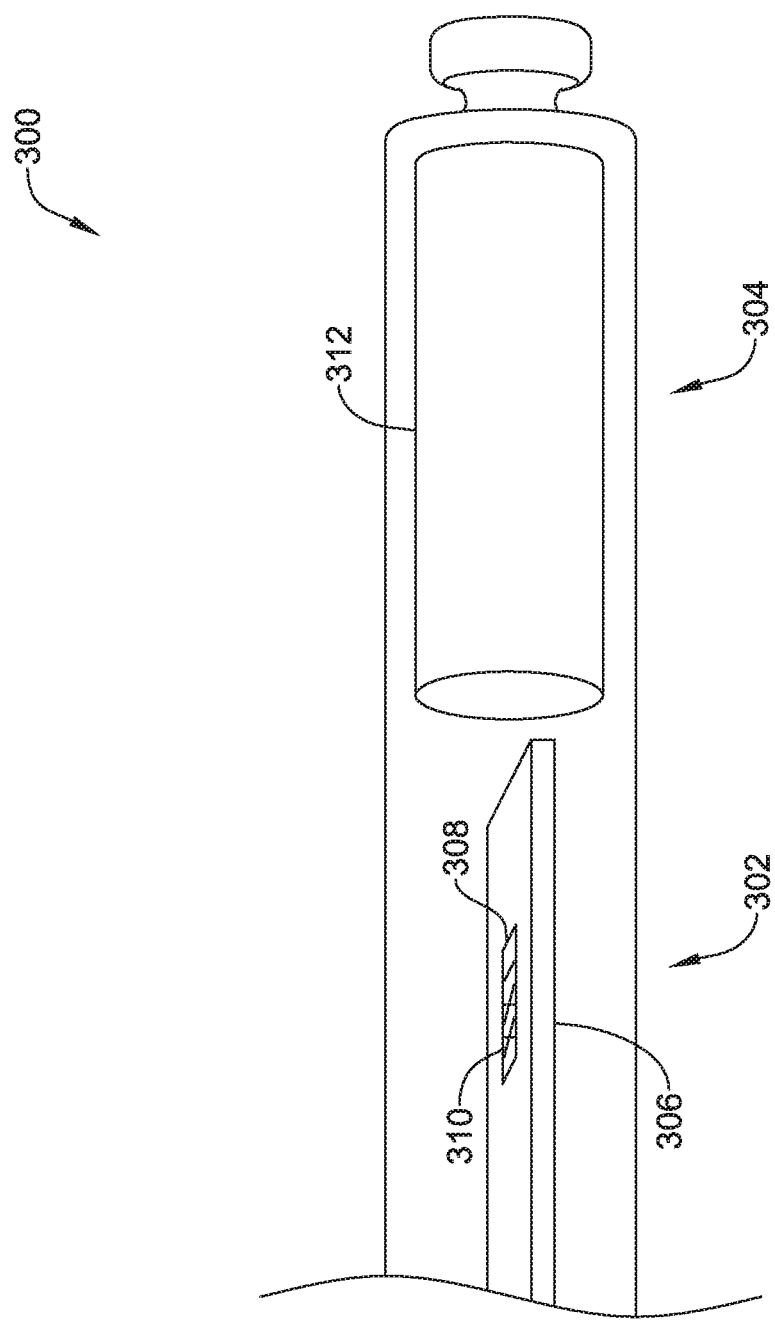
FIG. 21 is a schematic cutaway view of an illustrative leadless cardiac pacemaker, including an ID tag on a printed circuit board.

FIG. 21 is a schematic cutaway view of a leadless pacemaker 300, including a circuit section 302 and an energy storage section 304. A printed circuit board 306 is disposed within the circuit section 302 and in some instances may be a planar circuit board that is axially aligned within the circuit section 302. One or more (one is illustrated) ID tags 308 may be disposed on the printed circuit board 306 and may include radiopaque characters 310. The ID tag(s) 308 may be formed of any desired materials and using any particular techniques as described herein. An energy storage device 312 may be disposed within the energy storage section 304 and provides power to the printed circuit board 306.

Figure 22:
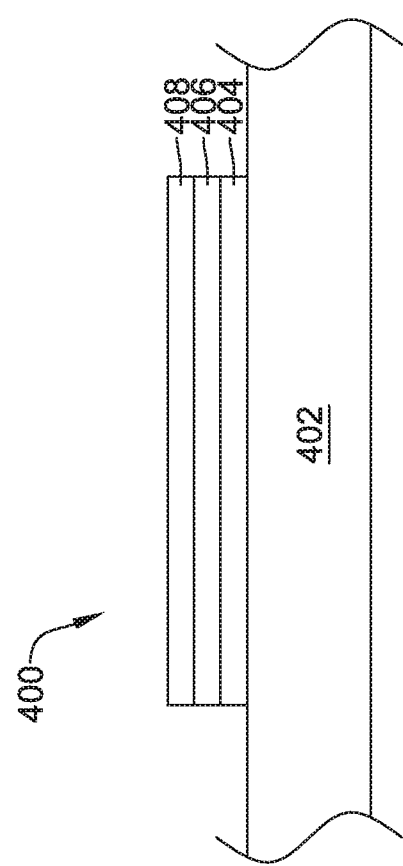
FIG. 22 is a schematic cross-sectional side view of an illustrative radiopaque ID tag.
Figure 23:
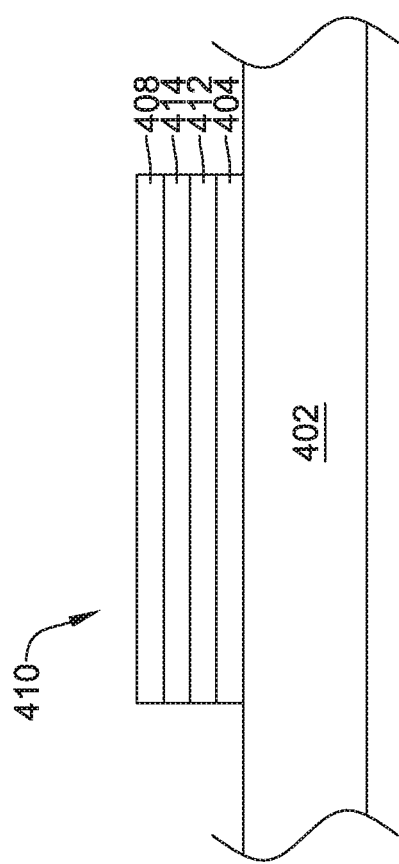
FIG. 23 is a schematic cross-sectional side view of another illustrative radiopaque ID tag.
Figure 24:
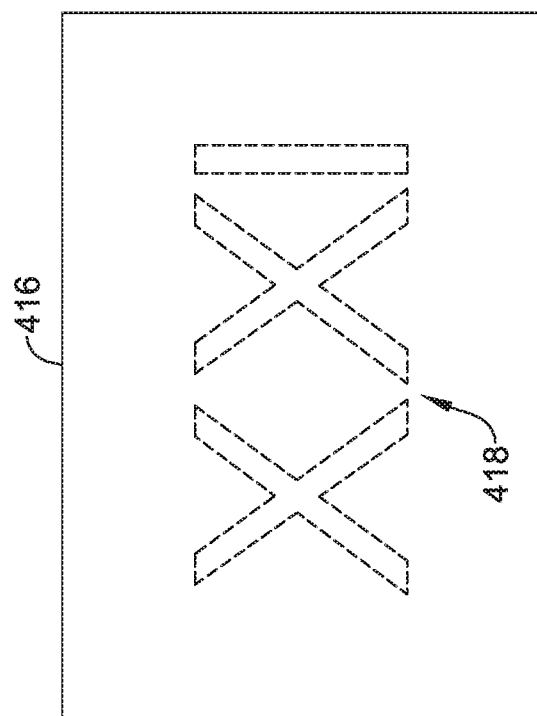
FIG. 24 is a schematic top view of the radiopaque ID tags of FIGS. 22 and 23.

The previous Figures illustrate various parts of an implantable medical device, such as a leadless pacemaker, that include one or more radiopaque ID tags that are secured relative to the part, or formed within the part. FIGS. 22-24 provide illustrative but non-limiting examples of the construction of a radiopaque ID tag.

FIG. 22 is a schematic cross-sectional side view of an illustrative radiopaque ID tag 400. The illustrative ID tag 400 is formed on a substrate 402. The substrate 402 may, for example, be alumina, silicon or glass. In the example shown, a polyimide layer 404 is formed on the substrate 402 in any suitable manner, such as spin coating. In some cases, the polyimide layer 404 may have a thickness that is about 7 to 10 microns, but this is not required. A radiopaque layer 406 is formed on the polyimide layer 404. The radiopaque layer 406 may be formed of any desired material, but in some cases may be tantalum, platinum or gold. In some cases, the radiopaque layer 406 may be formed via sputtering, gravure printing, screen printing, ink jet printing, vacuum evaporation, electron-assisted evaporation (EBPVD), thermal vapor evaporation, atomic layer deposition, and/or any other suitable process or technique. In some cases, the radiopaque layer 406 may have a thickness sufficient to provide adequate visibility during imaging processes such as x-ray. In some cases, the thickness may vary depending upon the specific material used for the radiopaque layer 406. Once the radiopaque layer 406 has been formed, the radiopaque layer 406 may be patterned and etched to form an identifiable character or characters that are visible under x-ray. If the radiopaque layer 406 is printed or otherwise patterned when formed, this patterning step may not be needed. In some cases, a polyimide layer 408 may be formed on top of the radiopaque layer 406. The radiopaque ID tag 400 may be removed from the substrate 402.

FIG. 23 is a schematic cross-sectional side view of another illustrative radiopaque ID tag 400. The ID tag 410 is formed on a substrate 402. The substrate 402 may, for example, be alumina, silicon or glass. In the example shown, a polyimide layer 404 is formed on the substrate 402 in any suitable manner, such as spin coating. In some cases, the polyimide layer 404 may have a thickness that is about 7 to 10 microns, but this is not required. An adhesion layer 412 may be applied over the polyimide layer 404. In some cases, the adhesion layer 412 is titanium, but this is not required. The adhesion layer 412 may be used to help improve adhesion between the radiopaque layer 414 and the polyimide layer 404. In the example shown, a radiopaque layer 414 is sputtered or otherwise applied over the adhesion layer 412. In some cases, the radiopaque layer 414 is tantalum, platinum or gold. However, it is contemplated that the radiopaque layer 414 may be any suitable radiopaque material. Once the radiopaque layer 414 has been formed, the radiopaque layer 414 may be patterned and etched to form an identifiable character or characters that are visible under x-ray. If the radiopaque layer 414 is printed or otherwise patterned when formed, this patterning step may not be needed. In some cases, a polyimide layer 408 may be formed on top of the radiopaque layer 414. When desired, a second adhesion layer (not shown) may be provided over the radiopaque layer 414 and under the polyimide layer 408 to help improve adhesion between the radiopaque layer 414 and the polyimide layer 408. The radiopaque ID tag 410 may be removed from the substrate 402. While polyimide is used for layers 404, 408 in the illustrative radiopaque ID tag 400 and 410, it is contemplated that any suitable material may be used for these layers. Moreover, it is contemplated that additional layers may be provided if desired.

FIG. 24 is a schematic top view of the illustrative radiopaque ID tag 400 (or 410, as it will be appreciated that these tags would appear the same from the top). The illustrative radiopaque ID tag 400, 410 has a top surface 416. A set of characters 418 are visible via x-ray when viewed from the top surface 416. As illustrated, the set of characters 418 reads "XX1", but this is merely illustrative and is not intended to be limiting in any fashion. In some cases, the set of characters 418 may include alphanumeric characters, a one or two dimensional bar code, and/or any other suitable marking as desired. In some cases, the set of characters 418 may identify a manufacturer and/or model number of an implanted device or component.

Figure 25:
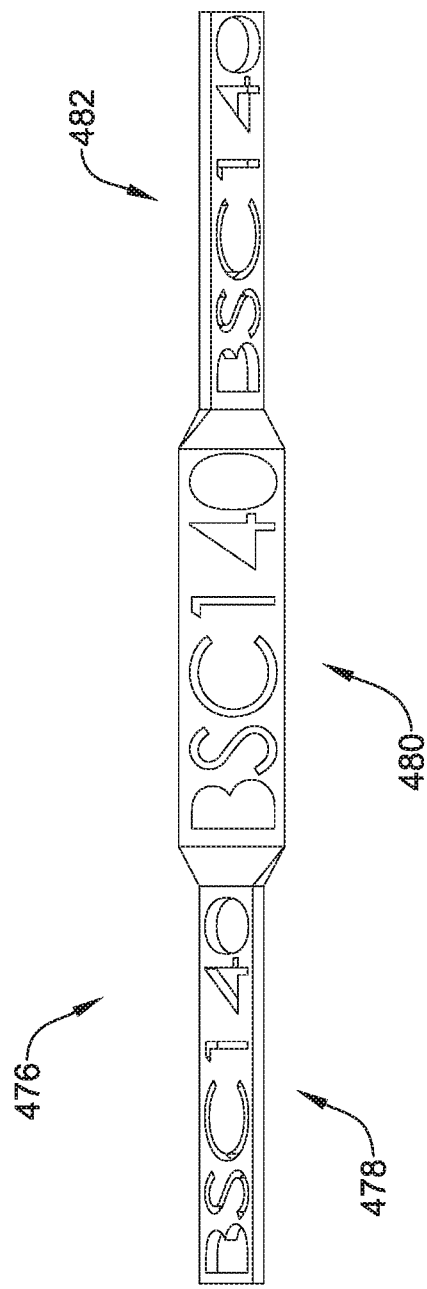
FIG. 25 is a perspective view of an illustrative battery cathode incorporating radiopaque ID tags formed therein.

FIG. 25 is a perspective view of an illustrative battery cathode 476 in accordance with an embodiment of the present disclosure. Unlike the cathode 76 (FIG. 7), which bears a first ID tag 76a and/or a second ID tag 76b that are secured to the cathode 76, or formed on or in a surface of the cathode 76, the cathode 476 is formed of a radiopaque material that has been twisted into several distinct planes. In the example shown in FIG. 25, the battery cathode 476 includes a first plane 478, a second plane 480 and a third plane 482, each rotated about 60 degrees from the adjacent plane, although the relative rotational position of each plane may be different depending on the application. In some embodiments, the battery cathode 476 may have just two planes, or could have four or more planes.

In the example shown, each plane 478, 480 and 482 includes one or more characters. As illustrated, the first plane 478 includes several characters 484, the second plane 480 includes several characters 486 and the third plane 482 includes several characters 488. As shown, each of the characters 484, 486 and 488 spell out "BSC 140", but this is merely illustrative. In some cases, the characters 484, 486 and 488 may all be different. In the example shown, the characters 484, 486 and 488 are each formed by cutting, etching or otherwise removing radiopaque material to form the characters 484, 486 and 488. In some cases, the characters 484, 486 and 488 are apertures that extends all the way through the battery cathode 476 as shown. In other cases, the characters 484, 486 and 488 are depressions that extends only part way through the battery cathode 476. In either cases, the characters 484, 486 and 488 may show up in an x-ray as relatively darker than the rest of the battery cathode 476. It will be appreciated that by creating each plane in a different orientation, it may be easier to read in an x-ray, regardless of the position of the device that includes the battery cathode 476.

In some instances, the battery cathode 476 may be made from a solid piece of radiopaque material. In other cases, the battery cathode 476 may be made from a non-radiopaque substrate that is coated with a radiopaque material. When the battery cathode 476 is made from a non-radiopaque substrate that is coated with a radiopaque material, the characters 484, 486 and 488 may be formed by etching through the radiopaque material to form an image of the characters 484, 486 and 488, or a reverse image of the characters 484, 486 and 488, under x-ray radiation, as desired.

While FIG. 25 shows an illustrative battery cathode 476, it is contemplated that a similar structure may function as a battery anode. In some cases, a similar structure may not form part of a battery at all. In some cases, a similar structure may serve as a conductor, a support structure or some other function within an implantable medical device. In some case, a similar structure may not perform any other function other than a radiopaque ID tag for an implantable medical device.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

We claim:

1. A leadless cardiac pacemaker comprising:
   an elongated housing including a length, an energy storage section and a circuit section, the energy storage section defining a first volume that extends along a first fraction of the length of the elongated housing and the circuit section defining a second volume that extends along a second fraction of the length of the elongated housing, wherein the first fraction does not overlap with the second fraction of the length of the elongated housing;
   an energy source disposed within the first volume;
   a circuit board disposed within the second volume but not in the first volume, the circuit board operably coupled to the energy source;
   a first electrode and a second electrode each exposed along an exterior of the elongated housing and operatively coupled to the circuit board; and
   an ID tag disposed on or in the circuit section of the elongated housing while not extending into the energy storage section, the ID tag configured to define a radiopaque manufacturer code that visually identifies a manufacturer of the leadless cardiac pacemaker.

2. The leadless cardiac pacemaker of claim 1, wherein the circuit section of the elongated housing has an inner surface that includes an insulative coating, and the ID tag is positioned between the inner surface of the circuit section of the elongated housing and the insulative coating.

3. The leadless cardiac pacemaker of claim 1, wherein the second volume houses a liner, wherein the ID tag engages the liner.

4. The leadless cardiac pacemaker of claim 3, wherein the circuit board has a first major surface and an opposing second major surface, and wherein the first major surface and the second major surface extend substantially perpendicular to the length of the elongated housing.

5. The leadless cardiac pacemaker of claim 4, wherein the liner extends circumferentially around at least part of the circuit board.

6. The leadless cardiac pacemaker of claim 1, wherein the ID tag is disposed within the second volume adjacent an inner wall of the elongated housing, wherein the ID tag is shaped to conform with the inner wall of the elongated housing.

7. The leadless cardiac pacemaker of claim 6, wherein the inner wall is curved, and the ID tag is curved to conform with the curved inner wall of the elongated housing.

8. The leadless cardiac pacemaker of claim 7, wherein the ID tag has a length and a width, where the length is longer than the width and the length of the ID tag extends along the length of the elongated housing, and wherein the width of the ID tag is curved to conform with the curved inner wall of the elongated housing.

9. The leadless cardiac pacemaker of claim 1, wherein the ID tag is disposed on or in the circuit board.

10. A leadless cardiac pacemaker, comprising:
an elongated housing including a length between a distal end and a proximal end, an energy storage section and a circuit section, the energy storage section defining a first volume that extends along a first fraction of the length of the elongated housing and the circuit section defining a second volume that extends along a second fraction of the length of the elongated housing, wherein the first fraction does not overlap with the second fraction of the length of the elongated housing;
two or more electrodes including:
  a distal electrode secured relative to the elongated housing;
  a proximal electrode secured relative to the elongated housing proximally of the distal electrode;
a fixation member extending distally of the distal end of the elongated housing;
an energy source disposed within the first volume of the elongated housing;
a circuit board disposed within the second volume, the circuit board operably coupled to the energy source and to the two or more electrodes;
an ID tag disposed on or in the circuit board in the circuit section while not extending into the energy storage section of the elongated housing, the ID tag configured to define a radiopaque manufacturer code that visually identifies a manufacturer of the leadless cardiac pacemaker.

11. The leadless cardiac pacemaker of claim 10, wherein the circuit board has a first major surface and an opposing second major surface, and wherein the first major surface and the second major surface extend substantially parallel with the length of the elongated housing.

12. The leadless cardiac pacemaker of claim 10, wherein the ID tag is a multi-layered ID tag that includes a radiopaque layer situated between two polymer layers.

13. The leadless cardiac pacemaker of claim 12, wherein the multi-layered ID tag is secured to the circuit board.

* * * * *